(12) United States Patent
Stromberg et al.

(10) Patent No.: US 9,957,226 B2
(45) Date of Patent: May 1, 2018

(54) ANTIMICROBIAL COMPOUNDS

(71) Applicant: AKTHELIA PHARMACEUTICALS, Reykjavik (IS)

(72) Inventors: Roger Stromberg, Hagersten (SE); Hakan Ottoson, Skarholmen (SE); Birgitta Agerberth, Stockholm (SE); Gudmundur Gudmundsson, Reykjavik (IS); Erica Miraglia, Stockholm (SE); Frank Nylen, Trangsund (SE)

(73) Assignee: Akthelia Pharmaceuticals, Reykjavik (IS)

( * ) Notice: Subject to any disclaimer, the term of this patent is extended or adjusted under 35 U.S.C. 154(b) by 0 days. days.

(21) Appl. No.: 15/033,686

(22) PCT Filed: Oct. 29, 2014

(86) PCT No.: PCT/IB2014/065678
§ 371 (c)(1),
(2) Date: May 2, 2016

(87) PCT Pub. No.: WO2015/063694
PCT Pub. Date: May 7, 2015

(65) Prior Publication Data
US 2016/0257642 A1 Sep. 8, 2016

(30) Foreign Application Priority Data
Oct. 31, 2013 (GB) .................................. 1319277.8

(51) Int. Cl.
*A61K 31/166* (2006.01)
*A61K 31/167* (2006.01)
*C07C 233/80* (2006.01)
*C07C 235/56* (2006.01)
*C07C 271/18* (2006.01)
*C07C 271/22* (2006.01)
*C07D 213/30* (2006.01)
*C07D 249/04* (2006.01)

(52) U.S. Cl.
CPC .......... *C07C 233/80* (2013.01); *A61K 31/166* (2013.01); *A61K 31/167* (2013.01); *C07C 235/56* (2013.01); *C07C 271/18* (2013.01); *C07C 271/22* (2013.01); *C07D 213/30* (2013.01); *C07D 249/04* (2013.01)

(58) Field of Classification Search
CPC combination set(s) only.
See application file for complete search history.

(56) References Cited

FOREIGN PATENT DOCUMENTS

WO 2010043953 A2 4/2010

OTHER PUBLICATIONS

Tamma et al., Clinical Microbiology Review, 2012.*
Mahiwal, K. et al., "Synthesis, antimicrobial evaluation, ot-QSAR and mt-QSAR studies of 2-amino benzoic acid derivatives," Med Chem Res (2010) 21(3):293-307.
Pochampally, J. et al., "Synthesis and molecular modelling studies of substituted novel aryl amide analogues and evaluation of their antimicrobial activity," World Journal of Pharmacy and Pharmaceutical Sciences (2014) 3(3):1908-1930.
International Search Report and Written Opinion for International Patent Application No. PCT/IB2014/065678 dated Feb. 9, 2015 (10 pages).
International Preliminary Report on Patentability for International Patent Application No. PCT/IB2014/065678 dated May 12, 2016 (7 pages).

* cited by examiner

*Primary Examiner* — Zohreh A Fay
(74) *Attorney, Agent, or Firm* — Andrus Intellectual Property Law, LLP

(57) ABSTRACT

The invention provides compounds for use in treating microbial infection in an animal. Example compounds include Pyridin-3-ylmethyl (4-((2-aminophenyl)-carbamoyl)benzyl) carbamate ("Entinostat"). The compounds can act via induction of the innate antimicrobial peptide defense system, and stimulation of autophagy.

27 Claims, 6 Drawing Sheets

ANTIMICROBIAL COMPOUNDS

CROSS-REFERENCE TO RELATED APPLICATIONS

Figure 1:
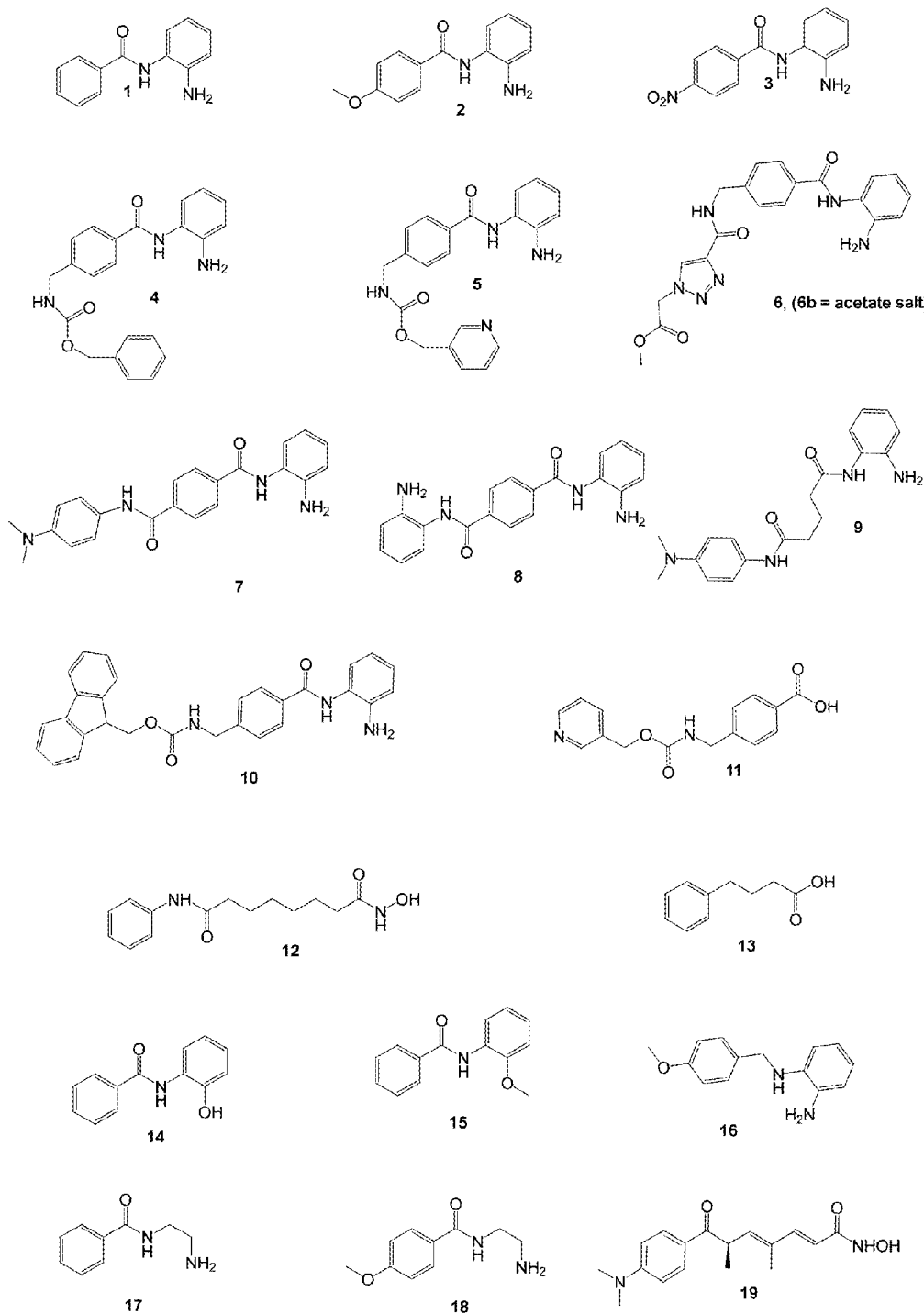

This patent application is a national stage filing under 35 U.S.C. 371 of International Application No. PCT/IB2014/065678, filed Oct. 29, 2014, which claims the benefit of priority of Great Britain Application No. GB1319277.8, filed Oct. 31, 2013, both of which are incorporated herein by reference in their entireties.

TECHNICAL FIELD

The invention relates to compounds which are useful for treatment of microbial infection, by stimulating the innate antimicrobial peptide system.

BACKGROUND ART

Innate immunity constitutes the front line of our defence system against microbes. Antimicrobial peptides (AMPs) are crucial components of innate defences that are synthesized constitutively and/or induced at epithelial surfaces, where the initial contact with microbes takes place (1). AMPs are widespread in nature, from fungi, plants and invertebrates to vertebrates, which establishes these defences are evolutionary conserved. AMPs possess broad activity against various pathogens, i.e. viruses, bacteria, fungi, and parasites (2). There are two major classes of AMPs in mammals, the defensins (α- and β-families) and the cathelicidins (3, 4). Besides the microbicidal activity (5), these peptides have been shown to act as chemo-attractants for cells of both the adaptive and innate immunity and to modulate immune responses (6-8). Thus, AMPs constitute a link between the innate and adaptive immunity.

The expression of AMPs can be induced by certain compounds. Butyrate (BA) was found to induce cathelicidin expression in epithelial cells (9). Moreover, sodium butyrate counteracted pathogen down-regulation of AMPs expression, resulting in pathogen elimination from epithelial surfaces in vivo in a rabbit model of Shigellosis (10). Phenylbutyrate (PBA), an analogue of butyrate, was shown to upregulate the expression of LL-37, the sole cathelicidin in humans, in epithelial cell lines and in monocytes (11). The active form of Vitamin D3, 1,25-dihydroxyvitamin D3, was also reported to enhance the expression of LL-37 in keratinocytes, immune cells, and in epithelial cells (12-14). Interestingly, PBA and 1,25-dihydroxyvitamin D3 were found to up-regulate LL-37 in a synergistic manner (11).

The continual emergence of antibiotic resistance among bacterial pathogens poses a great challenge to the public health. The pipeline of new antibiotics in drug development has yet to match this threat, since only few novel agents have been developed in the last decades (15, 16). Strengthening immune defences against pathogens by boosting the expression of our own "natural antibiotics" may represent novel or complementary pharmaceutical interventions in infectious diseases. Importantly, the multiplicity of AMPs with overlapping antibacterial mechanisms secures minimal risk of microbial resistance (17).

WO2009/087474 (Akthelia Pharmaceuticals) concerns generally the use of phenylbutyrate and similar compounds and their glycerol esters, and other compounds including vitamin D, for treating, preventing or counteracting microbial infections in animals by stimulating the innate antimicrobial peptide defence system, such as LL-37 in humans. Preferred compounds include phenyl substituted butyrate derivatives. This publication describes, inter alia, how CAP-18 (the rabbit homologue to LL-37) is induced in the rabbit colonic epithelium following oral administration. The publication further describes the expression of LL-37 in a bronchial epithelial cell line VA10. The publication further describes the cure of rabbits from shigellosis.

WO2012/0140504 (Raqib et al) also relates to the use of compounds for stimulating the innate antimicrobial peptide defence system, such as LL-37 in humans, in particular novel targets, organs, cells or tissues.

WO2008/073174 (GALLO) describes methods and compositions for modulating gene expression and the innate immune response by use of 1,25(OH)$_2$ vitamin D3 (1,25D3). That compound is tested alongside non-specific histone deacetylase inhibitors (HDACi) including butyrate or trichostatin A.

US20080038374 (Stahle) describes use of a vitamin D compound, which is able to specifically and directly up-regulate hCAP18, for the manufacturing of a medicament with antimicrobial effect for treatment of conditions deficient in LL-37, such as chronical ulcers, and atopic dermatitis.

Liu et al "Toll-Like Receptor Triggering of a Vitamin D-Mediated Human Antimicrobial Response" 24 Mar. 2006 VOL 311 SCIENCE, pp 1770-1773, describes data which is said to support a link between TLRs and vitamin D-mediated innate immunity and suggest that differences in ability of human populations to produce vitamin D may contribute to susceptibility to microbial infection, such as *Mycobacterium tuberculosis*.

Hata et al. (2008) "*Administration of oral vitamin D induces cathelicidin production in atopic individuals*" J ALLERGY CLIN IMMUNOL, VOLUME 122, NUMBER 4, described a study in which 14 normal controls and 14 atopic subjects with moderate to severe atopic dermatitis were treated with oral vitamin D3 to see if this could overcome the relative deficiency in induction of cathelicidin in the atopic patients. After supplementation with 4000 IU/d oral vitamin D for 21 days, AD lesional skin showed a statistically significant increase in cathelicidin expression.

The synergistic effects of PBA and vitamin D has been demonstrated in vitro in the VA10 cell line in a publication by Steinmann et al (2009) ANTIMICROBIAL AGENTS AND CHEMOTHERAPY (53), 5127-5133.

Martineau et al (*Lancet* 2011; 377: 242-50) describes a Phase II study of TB patients treated with high dose vitamin D.

US 2002l0076393 A1 relates to a method for the stimulation of defensin production in eukaryotic cells such as, for example, mammalian cells and various organs, using isoleucine or active isomers or analogs thereof. It further relates to methods for the prevention and treatment of infections and other various disease states and in the stimulation of the immune system in various tissues in which defensins are found.

Despite the above disclosures, it will be appreciated that the provision of compounds or combinations of compounds for use in enhancing the innate immune response against organisms or diseases not previously identified targeted in this way, or in tissues over and above those previously identified, would provide a contribution to the art.

DISCLOSURE OF THE INVENTION

The invention provides a new class of compounds which are powerful inducers of LL-37. This has been demonstrated both in a recombinant cell-line screening containing a construct with luciferase coupled to the human cathelicidin gene CAMP (Nylen et. al., 2013) and confirmed in normal colonic epithelial cell culture (HT-29 cells). The compounds for use in the present invention are benzoylated phenylenediamines or derivatives or analogs thereof, as described in more detail hereinafter.

Preferred compounds are N-(2aminophenyl)benzamide, N-(2aminophenyl)-4-methoxybenzamide, N-(2aminophenyl)-4-nitrobenzamide, benzyl (4-((2-aminophenyl)carbamoyl)benzyl)carbamate, pyridin-3-ylmethyl (4-((2-aminophenyl)carbamoyl)benzyl)carbamate, methyl 2-(4-((4-((2-aminophenyl)carbamoyl)benzyl)carbamoyl)-1H-1,2,3-triazol-1-yl)acetate, and N-(2-aminophenyl)-4-((4-(dimethyl-λ4-azanyl)phenyl)amino)benzamide.

The present invention provides for the use of the compounds described herein for the treatment of infectious disease. Preferred microbial targets and diseases targeted by the present invention are described hereinafter.

This effectiveness of this new class of inducers is unexpected, and implies that these compounds and its analogs may work via different or additional stimulatory mechanisms to some of the previous compounds used to stimulate the innate antimicrobial defence system. Although some of the compounds are known to be histone deacetylase (HDAC) inhibitors, in the light of the results described herein, there appear to be no direct relationship between effectiveness (1050) for HDAC inhibition and stimulation of LL-37 expression suggesting that the induction occur mainly through another mechanism.

In particular aspects of the invention, there are provided methods for treatment (including prophylaxis) of a microbial infection in an animal using the compounds described herein.

The present invention further provides a compound as defined herein for use as a medicament for treating (e.g. counteracting down-regulation caused by several pathogens) microbial infections in humans and other animals by stimulating the innate antimicrobial peptide defense system.

The compounds of the present invention exhibit an antimicrobial effect by stimulating the innate antimicrobial peptide defense system.

Generally the use of the present invention will be such as to lead to secretion of the relevant peptide same onto an epithelial surface (e.g. in the gastrointestinal tract or in the lung). This in turn will lead to increased antimicrobial activity at the surface (and hence improvement of its barrier function) and treatment of the microbial infection and disease caused by it.

In addition, as shown in the Examples hereinafter, the compounds defined herein also stimulate autophagy, which is believed to be via induction of LL-37 or independently of that, thereby additionally contributing to the removal of microbial infection.

The microbial targets and diseases targeted by the present invention may be any believed to benefit therefrom. Preferred targets are described herein but include diseases such as pneumonia, tuberculosis, shigellosis and additional enteric infections (30, 31).

Aspects of the invention include a method for treating, preventing or counteracting microbial infections, including bacterial, viral, fungal and parasitic infections (also including infections by bacterial strains resistant to currently used antibiotics), by administering a medicament comprising a secretagogue-effective amount of at least one compound of the invention as defined herein.

In yet a further aspect, the invention provides a pharmaceutical composition for use in the methods described herein e.g. for treating, preventing or counteracting a microbial infection, including the above mentioned types, comprising an active ingredient being at least one compound of the invention, and typically at least one pharmaceutically acceptable excipient.

In yet a further aspect, the invention provides use of compounds of the invention in the preparation of a medicament for use in the methods described herein.

Some aspects and embodiments of the invention will now be described in more detail.

In one aspect, the invention provides compounds of general formula (I), for use in a method of treatment of a microbial infection in an animal:

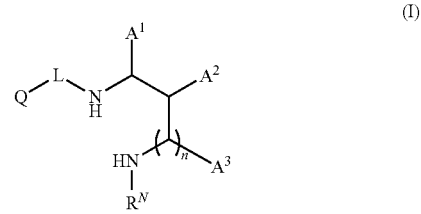

wherein:

Q is selected from Q1, Q2, Q3, Q4, Q5 and Q6:

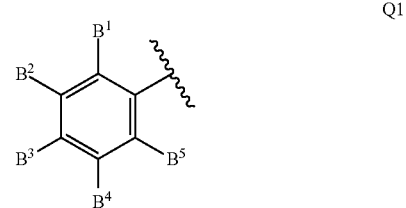

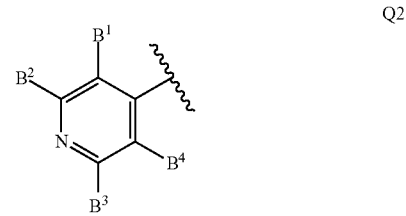

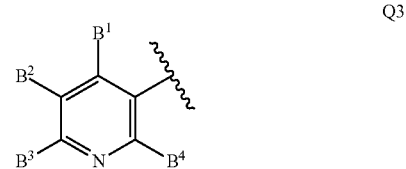

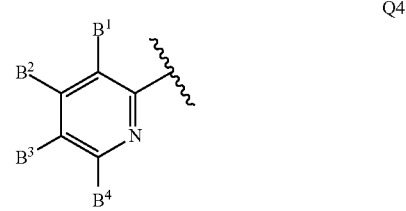

-continued

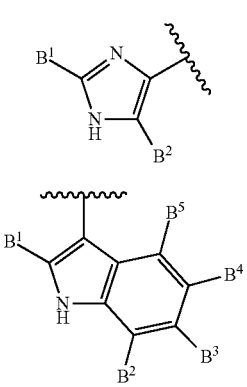

n is 0 or 1;

L is selected from —(CH$_2$)$_m$—, —C(=O)—, —(CH$_2$)$_m$—C(=O)—, —O—(CH$_2$)$_m$—C(=O)—, —O—C(=O)—(CH$_2$)$_m$—(C=O)—, —NH—C(=O)—, —NR—C(=O)—, —NH—(CH$_2$)$_m$—C(=O)—, —NR—(CH$_2$)$_m$—C(=O)—, —NH—C(=O)—(CH$_2$)$_m$—C(=O)—, —NR—C(=O)—(CH$_2$)$_m$—C(=O)—, —C(=O)—NH—(CH$_2$)$_m$—C(=O)—, and —(CH$_2$)$_m$—(CHR$^L$)—C(=O)—, where m is an integer from 1 to 4;

A$^1$ and A$^2$, together with the atoms to which they are bound, form an optionally substituted C$_{6-14}$aryl or heteroaryl group;

A$^3$, if present, is selected from H and optionally substituted C$_{1-4}$alkyl;

R$^N$ is selected from H and optionally substituted$^3$ C$_{1-4}$alkyl;

one of B$^1$, B$^2$, B$^3$, B$^4$, and B$^5$ is a group of formula —X—R$^X$ and the others are independently selected from H and R$^B$;

wherein each —R$^B$ is independently selected from halogen, —CF$_3$, —R, —OH, —OR, —OCF$_3$, —C(=O)OH, —C(=O)OR, —C(=O)R, —OC(=O)R, —NH$_2$, —NHR, —NR$_2$, —NO$_2$, —C(=O)NH$_2$, —C(=O)NHR, C(=O)NR$_2$, —S(=O)R, —S(=O)$_2$R, —S(=O)$_2$NR$_2$, or —CN;

X is selected from a covalent bond or C$_{1-3}$alkylene;

R$^X$ is selected from —H, R$^{XX}$ or R$^{XY}$;

wherein:

R$^{XX}$ is halogen, —CF$_3$, —OH, —OR, —OCF$_3$, —C(=O)OH, —NO$_2$, —NH$_2$, —NHR, —NR$_2$, —C(=O)NH$_2$, —C(=O)NR$_2$, —S(=O)R, —S(=O)$_2$R, —S(=O)$_2$NR$_2$, or —CN; and R$^{XY}$ is a group of formula -L$^X$-R$^{YY}$;

wherein L$^X$ is selected from:

—NH—C(=O)—O—, —NH—C(=O)—NH—, —NH—C(=O)—

—O—C(=O)—NH—, —O—C(=O)—O—, —O—(C=O)—

—C(=O)—NH—, —C(=O)—O—, —C(=O)—;

and R$^{YY}$ is selected from C$_{1-4}$alkyl, C$_{3-6}$cycloalkyl, —C$_{6-14}$aryl, -L$^Y$-C$_{6-14}$aryl, -L$^Y$-O—C$_{6-14}$aryl, —C$_{5-6}$heteroaryl, -L$^Y$-C$_{5-6}$heteroaryl, and -L$^Y$-O—C$_{5-6}$heteroaryl, wherein -L$^Y$- is C$_{1-3}$alkylene and wherein each of said groups is optionally substituted;

R$^L$ is selected from halogen, —R$^{LL}$, —CF$_3$, —OH, —OR$^{LL}$, —NO$_2$, —NH$_2$, —NHR$^{LL}$, —NR$_2$, —NH—C(=O)—R$^{LL}$, —NH—C(=O)—O—R$^{LL}$ wherein R$^{LL}$ is selected from —C$_{1-4}$alkyl, —C$_{3-6}$cycloalkyl, -Ph, -L$^L$-Ph, —C$_{5-6}$heteroaryl, -L$^L$-C$_{5-6}$heteroaryl wherein -L$^L$- is C$_{1-3}$alkylene.

and wherein each R is independently C$_{1-4}$alkyl.

FURTHER DESCRIPTION AND PREFERENCES

Group Q

In the compounds of formula (I), the group Q is selected from Q1, Q2, Q3, Q4, Q5 and Q6:

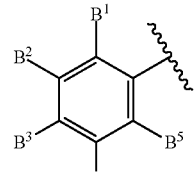
Q1

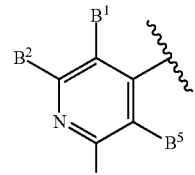
Q2

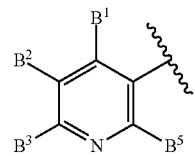
Q3

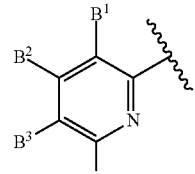
Q4

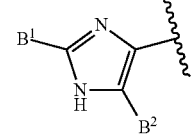
Q5

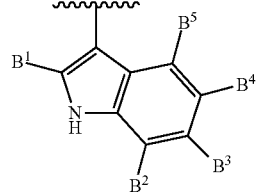
Q6 wherein one of B$^1$ and B$^2$ (and B$^3$, B$^4$ and B$^5$ where present) is a group of formula —X—R$^X$ and the others are independently selected from H and R$^B$. In other words, each possible Q group includes one —X—R$^X$ substituent in an available position, the other available positions being either unsubstituted (—H) or substituted with a group —R$^B$.

In some embodiments, Q is a phenyl group, Q1:

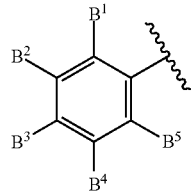

wherein one of $B^1$, $B^2$, $B^3$, $B^4$ and $B^5$ is a group of formula —X—$R^X$ and the others are independently selected from H and $R^B$.

In some embodiments, $B^3$ is a group of formula —X—$R^X$ and $B^1$, $B^2$, $B^4$ and $B^5$ are independently selected from H and $R^B$. Accordingly, in these embodiments, Q is a group of formula:

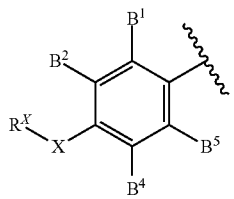

In other embodiments, $B^2$ is a group of formula —X—$R^X$ and $B^1$, $B^3$, $B^4$ and $B^5$ are independently selected from H and $R^B$. In still further embodiments, $B^1$ is a group of formula —X—$R^X$ and $B^2$, $B^3$, $B^4$ and $B^5$ are independently selected from H and $R^B$.

In some embodiments, one of $B^1$, $B^2$, $B^3$, $B^4$ and $B^5$ is a group of formula —X—$R^X$ and the others are independently H.

In some embodiments $B^2$ or $B^3$ is a group of formula —X—$R^X$ and the others are independently H.

In some embodiments $B^3$ is a group of formula —X—$R^X$ and the others are independently H.

In some embodiments, Q is a pyridyl group Q2, Q3 or Q4:

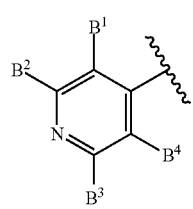

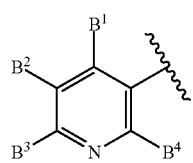

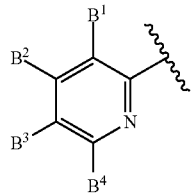

wherein one of $B^1$, $B^2$, $B^3$ and $B^4$ is a group of formula —X—$R^X$ and the others are independently selected from H and $R^B$.

In some embodiments, one of $B^1$, $B^2$, $B^3$ and $B^4$ is a group of formula —X—$R^X$ and the others are independently H. In some of said embodiments X is a covalent bond and $R^X$ is —H.

In some embodiments, Q is Q2.
In some embodiments, Q is Q3.
In some embodiments, Q is Q4.
In some embodiments, Q is an imidazolyl group Q5:

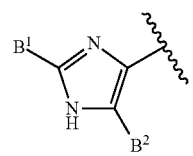

wherein one of $B^1$ and $B^2$ is a group of formula —X—$R^X$ and the other is selected from H and $R^B$.

In some embodiments, one of $B^1$ and $B^2$ is a group of formula —X—$R^X$ and the other is —H.

In some of said embodiments X is a covalent bond and $R^X$ is —H.

In some embodiments Q is an indolyl group Q6:

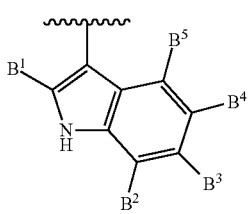

wherein one of $B^1$, $B^2$, $B^3$, $B^4$ and $B^5$ is a group of formula —X—$R^X$ and the others are independently selected from H and $R^B$.

In some embodiments, one of $B^1$, $B^2$, $B^3$, $B^4$ and $B^4$ is a group of formula —X—$R^X$ and the others are independently H. In some of said embodiments X is a covalent bond and $R^X$ is —H.

Group $R^B$

Where present, each —$R^B$ group is independently selected from halogen, —$CF_3$, —R, —OH, —OR, —$OCF_3$, —C(=O)OH, —C(=O)OR, —C(=O)R, —OC(=O)R, —$NH_2$, —NHR, —$NR_2$, —$NO_2$, —C(=O)$NH_2$, —C(=O)NHR, C(=O)$NR_2$, —S(=O)R, —S(=O)$_2$R, —S(=O)$_2$$NR_2$, or —CN.

In some embodiments, —$R^B$ is selected from halogen (i.e. —F, —Cl, —Br, —I), —$CF_3$, —R, —OH, —OR, —$NH_2$, —NHR, —$NR_2$, —$NO_2$, and —CN.

In some embodiments, —R$^B$ is selected from —OH, —OR, —NH$_2$, —NHR, and —NR$_2$.

In some embodiments, —R$^B$ is selected from —OH or —OR.

In some embodiments. —R$^B$ is —OR.

In some embodiments, —R$^B$ is —OMe.

In some embodiments, —R$^B$ is —R.

In some embodiments. —R$^B$ is -Me.

Group X—R$^X$

In the group —X—R$^X$, X is selected from a covalent bond or C$_{1-3}$alkylene and R$^X$ is selected from H, R$^{XX}$ or R$^{XY}$.

In some embodiments, X is a covalent bond (i.e. the group —X—R$^X$ is a group of formula —R$^X$).

In some embodiments, X is selected from C$_{1-3}$alkylene.

In some embodiments, X is selected from —CH$_2$—, —CH$_2$CH$_2$—, —CH$_2$CH$_2$CH$_2$—, —CH(CH$_3$)—, —CH(CH$_3$)CH$_2$—, —CH$_2$CH(CH$_3$)—, or —CH(CH$_2$CH$_3$)—.

In some embodiments, X is —CH$_2$—.

In some embodiments R$^X$ is H.

In some embodiments, R$^X$ is R$^{XX}$. R$^{XX}$ is selected from halogen, —CF$_3$, —OH, —OR, —OCF$_3$, —C(=O)OH, —NO$_2$, —NH$_2$, —NHR, —NR$_2$, —C(=O)NH$_2$, —C(=O)NR$_2$, —S(=O)R, —S(=O)$_2$R, —S(=O)$_2$NR$_2$, and —CN.

In some embodiments, R$^{XX}$ is selected from —OH, —OR, —NO$_2$, —NH$_2$, NHR, and —NR$_2$.

In some embodiments, R$^{XX}$ is selected from —OR, —NO$_2$ and —NR$_2$.

In some embodiments, R$^{XX}$ is —OMe, —NO$_2$, or —NMe$_2$.

In some embodiments, R$^X$ is R$^{XY}$ wherein R$^{XY}$ is a group of formula -L$^X$-R$^{YY}$.

L$^X$ is selected from —NH—C(=O)—O—, —NH—C(=O)—NH—, —NH—C(=O)—, —O—C(=O)—NH—, —O—C(=O)—O—, —O—(C=O)—, —C(=O)—NH—, —C(=O)—O—, and —C(=O)—.

In some embodiments, L$^X$ is selected from —NH—C(=O)—O—, —NH—C(=O)—, and —C(=O)—NH—.

In some embodiments, L$^X$ is —NH—C(=O)—O—.

In some embodiments, L$^X$ is —NH—C(=O)—.

In some embodiments, L$^X$ is —C(=O)—NH—.

R$^{YY}$ is selected from C$_{1-4}$alkyl, C$_{3-6}$cycloalkyl, —C$_{6-14}$aryl, -L$^Y$-C$_{6-14}$aryl, -L$^Y$-O—C$_{6-14}$aryl —C$_{5-6}$heteroaryl, -L$^Y$-C$_{5-6}$heteroaryl, and -L$^Y$-O—C$_{5-6}$heteroaryl, wherein -L$^Y$- is C$_{1-3}$alkylene and wherein each of said R$^{YY}$ groups is optionally substituted.

In some embodiments, R$^{YY}$ is independently: —C$_{6-14}$aryl, -L$^Y$-C$_{6-14}$aryl, —C$_{5-6}$heteroaryl, or -L$^Y$-C$_{5-6}$heteroaryl, wherein said C$_{6-14}$aryl and C$_{5-6}$heteroaryl groups are optionally substituted.

In some embodiments, R$^{YY}$ is independently: -Ph, -L$^Y$-Ph, C$_{5-6}$heteroaryl, or -L$^Y$-C$_{5-6}$heteroaryl, wherein said Ph and C$_{5-6}$heteroaryl groups are optionally substituted.

In some embodiments, R$^{YY}$ is independently: -L$^Y$-Ph or -L$^Y$-C$_{5-6}$heteroaryl, wherein said Ph and C$_{5-6}$heteroaryl groups are optionally substituted.

In some embodiments, R$^{YY}$ is independently- L$^Y$-C$_{6-14}$aryl, wherein said C$_{6-14}$aryl is optionally substituted.

In some embodiments, R$^{YY}$ is independently: -L$^Y$-Ph, wherein said Ph is optionally substituted.

In some embodiments, R$^{YY}$ is independently:

In some embodiments, -L$^Y$- is independently selected from —CH$_2$—, —CH$_2$CH$_2$—, —CH$_2$CH$_2$CH$_2$—, —CH(CH$_3$)—, —CH(CH$_3$)CH$_2$—, —CH$_2$CH(CH$_3$)—, and —CH(CH$_2$CH$_3$)—.

In some embodiments, -L$^Y$- is independently —CH$_2$—.

In some embodiments each of said R$^{YY}$ groups is optionally substituted with one or more substituents selected from: —F, —Cl, —Br, —I, —R, —CF$_3$, —OH, —OR, —OCF$_3$, —NO$_2$, -L$^{YY}$-OH, -L$^{YY}$-OR, —NH$_2$, —NHR, —NR$_2$, -L-NH$_2$, -L-NHR, -L$^{YY}$-NR$_2$, —CO$_2$H, —CO$_2$R, -L$^{YY}$-CO$_2$H, -L$^{YY}$-CO$_2$R, -Ph, and -L$^{YY}$-Ph-, wherein L$^{YY}$ is C$_{1-3}$alkylene.

In some embodiments, each of said R$^{YY}$ groups is optionally substituted with one or more substituents selected from: —OH, —OR, -L-OH, -L-OR, —NH$_2$, —NHR, —NR$_2$, -L$^{YY}$-NH$_2$, -L$^{YY}$-NHR, -L$^{YY}$-NR$_2$, -L$^{YY}$-CO$_2$H, -L$^{YY}$-CO$_2$R, -Ph, and -L$^{YY}$-Ph-, wherein L$^{YY}$ is C$_{1-3}$alkylene.

In some embodiments, each of said R$^{YY}$ groups is optionally substituted with one or more substituents selected from —NH$_2$, —NHR, —NR$_2$, -L$^{YY}$-CO$_2$H, and -L-CO$_2$R, wherein L$^{YY}$ is C$_{1-3}$alkylene.

In some embodiments, R$^{YY}$ is independently: -L$^Y$-Ph, wherein said Ph is substituted with one or more substituents selected from: —OH, —OR, -L$^{YY}$-OH, -L$^{YY}$-OR, —NH$_2$, —NHR, —NR$_2$, -L$^{YY}$-NH$_2$, -L$^{YY}$-NHR, -L$^{YY}$-NR$_2$, -L-CO$_2$H, -L$^{YY}$-CO$_2$R, -Ph, and -L$^{YY}$-Ph-, wherein L$^{YY}$ is C$_{1-3}$alkylene.

In some embodiments, R$^{YY}$ is independently: -L$^Y$-Ph, wherein said Ph is substituted with one or more substituents selected from: —NH$_2$, —NHR, and —NR$_2$.

In some embodiments, R$^{YY}$ is independently: —C$_{5-6}$heteroaryl, wherein said C$_{5-6}$heteroaryl is substituted with one or more substituents selected from: —OH, —OR, -L-OH, -L$^{YY}$-OR, —NH$_2$, —NHR, —NR$_2$, -L$^{YY}$-NH$_2$, -L$^{YY}$-NHR, -L$^{YY}$-NR$_2$, -L$^{YY}$-CO$_2$H, -L$^{YY}$-CO$_2$R, -Ph, and -L$^{YY}$-Ph-, wherein L$^{YY}$ is C$_{1-3}$alkylene.

In some embodiments, R$^{YY}$ is independently: —C$_{5-6}$heteroaryl, wherein said C$_{5-6}$heteroaryl is substituted with -L$^{YY}$-CO$_2$R.

In some embodiments, -L- is independently selected from —CH$_2$—, —CH$_2$CH$_2$—, —CH$_2$CH$_2$CH$_2$—, —CH(CH$_3$)—, —CH(CH$_3$)CH$_2$—, —CH$_2$CH(CH$_3$)—, and —CH(CH$_2$CH$_3$)—.

In some embodiments, -L$^{YY}$- is independently —CH$_2$—.

Linker L

In the compounds of formula (I), the linker group L is selected from —(CH$_2$)$_m$—, —C(=O)—, —(CH$_2$)$_m$—C(=O)—, —O—(CH$_2$)$_m$—C(=O)—, —O—C(=O)—(CH$_2$)$_m$—(C=O)—, —NH—C(=O)—, —NR—C(=O)—, —NH—(CH$_2$)$_m$—C(=O)—, —NR—(CH$_2$)$_m$—C(=O)—, —NH—C(=O)—(CH$_2$)$_m$—C(=O)—, —NR—C(=O)—(CH$_2$)$_m$—C(=O)—, —C(=O)—NH—(CH$_2$)$_m$—C(=O)—, and —(CH$_2$)$_m$—(CHR$^L$)—C(=O)—, where m is an integer from 1 to 4.

In some embodiments, L is selected from —(CH$_2$)$_m$—, —C(=O)—, —(CH$_2$)$_m$—C(=O)—, —NH—C(=O)—, —NR—C(=O)—, —NH—C(=O)—(CH$_2$)$_m$—C(=O)—, —C(=O)—NH—(CH$_2$)$_m$—C(=O)—, and —(CH$_2$)$_m$—(CHR$^L$)—C(=O)—.

In some embodiments, L is selected from —(CH$_2$)$_m$—, —C(=O)—, —NH—C(=O)—, and —NR—C(=O)—.

In some embodiments, L is —C(=O)—. Accordingly, the compound may be a compound of formula (II):

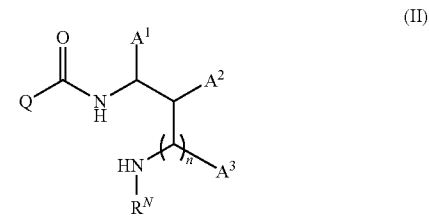

(II)

In some embodiments, L is —C(=O)—NH—(CH$_2$)$_m$—C(=O)—. Accordingly, the compound may be a compound of formula (III):

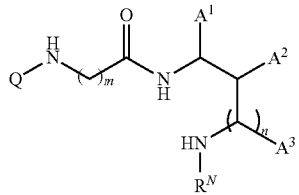

(III)

In some embodiments, L is —(CH$_2$)$_m$—(CHR$^L$)—C(=O)—, wherein R$^L$ is as defined herein. Accordingly, the compound may be a compound of formula (IV):

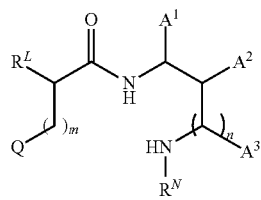

(IV)

Group R$^L$

Where present, e.g. in compounds of formula (Ic), the group R$^L$ is selected from halogen, —R$^{LL}$, —CF$_3$, —OH, —OR$^{LL}$, —NO$_2$, —NH$_2$, —NHR$^{LL}$, —NR$_2$, —NH—C(=O)—R$^{LL}$, —NH—C(=O)—O—R$^{LL}$.

In some embodiments, R$^L$ is selected from —NH$_2$, —NHR$^{LL}$, —NH—C(=O)—R$^{LL}$ and —NH—C(=O)—O—R$^{LL}$, wherein R$^{LL}$ is as previously defined.

In some embodiments, R$^L$ is NH$_2$.

In some embodiments, R$^L$ is —NHR$^{LL}$.

In some embodiments, R$^L$ is —NH—C(=O)—O—R$^{LL}$.

R$^{LL}$ is selected from —C$_{1-4}$alkyl, —C$_{3-6}$cycloalkyl, -Ph, -L$^L$-Ph, —C$_{5-6}$heteroaryl, and -L$^L$-C$_{5-6}$heteroaryl wherein -L$^L$- is C$_{1-3}$alkylene, wherein said -Ph and —C$_{5-6}$heteroaryl are optionally substituted.

In some embodiments said -Ph and —C$_{5-6}$heteroaryl are optionally substituted with one or more groups selected from: —F, —Cl, —Br, —I, —R, —CF$_3$, —OH, —OR, —OCF$_3$, —NO$_2$, —NH$_2$, —NHR, —NR$_2$, —CO$_2$H, —CO$_2$R.

In some embodiments, R$^{LL}$ is selected from -Ph, -L$^L$-Ph, —C$_{5-6}$heteroaryl, and -L$^L$-C$_{5-6}$heteroaryl.

In some embodiments, R$^{LL}$ is selected from -L$^L$-Ph and -L$^L$-C$_{5-6}$heteroaryl.

In some embodiments, R$^{LL}$ is -L$^L$-Ph.

In some embodiments, R$^{LL}$ is —CH$_2$-Ph (-Bn).

L$^L$ is selected from C$_{1-3}$ alkylene.

In some embodiments, L$^L$ is selected from:
—CH$_2$—, —CH$_2$CH$_2$—, —CH$_2$CH$_2$CH$_2$—,
—CH(CH$_3$)—, —CH(CH$_3$)CH$_2$—, —CH$_2$CH(CH$_3$)—,
or —CH(CH$_2$CH$_3$)—.

In some embodiments L$^L$ is —CH$_2$— or —CH$_2$CH$_2$—.

In some embodiments L$^L$ is —CH$_2$—.

Group R$^N$

R$^N$ is selected from H and optionally substituted C$_{1-4}$alkyl.

In some embodiments, R$^N$ is H.

In some embodiments, R$^N$ is C$_{1-4}$alkyl.

In some embodiments, when R$^N$ is C$_{1-4}$alkyl, said C$_{1-4}$alkyl is optionally substituted with one or more substituents R$^{N1}$, wherein each R$^{N1}$ is independently selected from halogen, —CF$_3$, —R, —OH, —OR, —OCF$_3$, —NH$_2$, —NHR, —NR$_2$, —NO$_2$ and —CN, wherein each R is independently C$_{1-4}$alkyl.

In some embodiments, R$^{N1}$ is independently selected from —OH, —OR, —NH$_2$, —NHR, —NR$_2$.

In some embodiments, R$^{N1}$ is OH or NH$_2$.

In some embodiments R$^{N1}$ is NH$_2$.

In some embodiments, R$^N$ is selected from methyl, ethyl, n-propyl, iso-propyl, n-butyl, iso-butyl, sec-butyl, and tert-butyl and is optionally substituted.

In some embodiments, R$^N$ is ethyl and is optionally substituted.

In some embodiments, R$^N$ is ethyl, substituted with at least one R$^{N1}$.

In some embodiments, R$^N$ is —CH$_2$CH$_2$NH$_2$.

Groups A$^1$, A$^2$, A$^3$

In some embodiments, A$^1$ and A$^2$, together with the atoms to which they are bound, form an optionally substituted C$_{6-14}$aryl group.

In some embodiments, said C$_{6-14}$aryl group is optionally substituted with one or more substituents R$^{A2}$, wherein each R$^{A2}$ is independently selected from halogen, —CF$_3$, —R, —OH, —OR, —OCF$_3$, —NO$_2$, —C(=O)OH, —C(=O)OR, —C(=O)R, —OC(=O)R, —NH$_2$, —NHR, —NR$_2$, —C(=O)NH$_2$, —C(=O)NHR, —C(=O)NR$_2$, —S(=O)R, —S(=O)$_2$R, —S(=O)$_2$NR$_2$, and —CN.

In some embodiments, R$^{A2}$ is independently selected from —R, —OH, —OR, —OCF$_3$, —NO$_2$, —NH$_2$, —NHR, —NR$_2$, and —CN.

In some embodiments, R$^{A2}$ is independently —R.

In some embodiments, R$^{A2}$ is independently methyl.

In some embodiments, A$^1$ and A$^2$, together with the atoms to which they are bound, form an optionally substituted phenyl group. Accordingly, the compound may be a compound of formula (V):

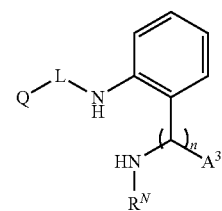

(V)

In some embodiments, A$^1$ and A$^2$, together with the atoms to which they are bound, form an optionally substituted naphthalene group. Accordingly, the compound may be a compound of formula (VI):

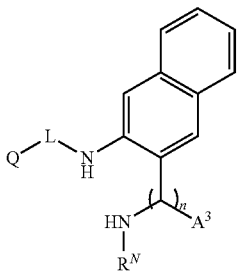

(VI)

In the compounds of formula (V) and (VI) the phenyl and naphthalene rings may optionally be substituted with one or more substituents $R^{A2}$ as defined above.

In some embodiments, $A^1$ and $A^2$, together with the atoms to which they are bound, form an unsubstituted phenyl or naphthalene group.

In some embodiments, $A^1$ and $A^2$, together with the atoms to which they are bound, form an unsubstituted phenyl group.

In some embodiments, $A^1$ and $A^2$, together with the atoms to which they are bound, form a phenyl substituted with one or more substituents $R^{A2}$.

In some embodiments, $A^1$ and $A^2$, together with the atoms to which they are bound, form a phenyl substituted with two substituents $R^{A2}$.

$A^3$, if present, is selected from H and optionally substituted $C_{1-4}$alkyl.

In some embodiments, $A^3$ is H.

In some embodiments, $A^3$ is selected from methyl, ethyl, n-propyl, iso-propyl, n-butyl, iso-butyl, sec-butyl, and tert-butyl.

In some embodiments, $A^3$ is methyl or ethyl.

In some embodiments, $A^3$ is methyl.

n is selected from 0 and 1. When n is 0, $A^3$ (and the atom to which it is attached) is absent.

Accordingly, the compound may be a compound of formula (VII):

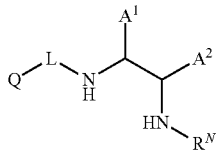

(VII)

Groups R

Each 'R', as used throughout these definitions, is independently a $C_{1-4}$ alkyl group.

In some embodiments, R is selected from methyl, ethyl, n-propyl, iso-propyl, n-butyl, iso-butyl, sec-butyl, and tert-butyl.

In some embodiments, R is methyl or ethyl.

In some embodiments, R is methyl.

CERTAIN PREFERRED EMBODIMENTS

In some embodiments:
$A^1$ and $A^2$, together with the atoms to which they are bound, form a phenyl ring, optionally substituted with one or more substituents $R^{A2}$;
n is 0;
$R^N$ is H.

Accordingly, the compound is a compound of formula (VIII):

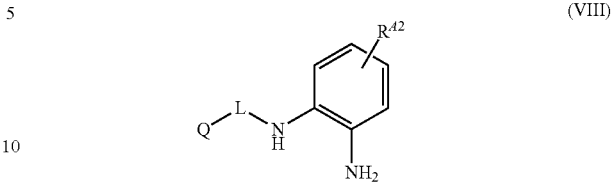

(VIII)

wherein Q, L and $R^{A2}$ are as previously defined.

In some embodiments:
$A^1$ and $A^2$, together with the atoms to which they are bound, form a phenyl ring, optionally substituted with one or more substituents $R^{A2}$;
n is 0;
$R^N$ is H;
L is C(=O).

Accordingly, the compound is a compound of formula (IX):

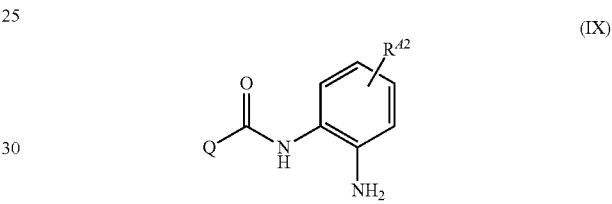

(IX)

wherein Q and $R^{A2}$ are as previously defined.

In some embodiments:
$A^1$ and $A^2$, together with the atoms to which they are bound, form a phenyl ring, optionally substituted with one or more substituents $R^{A2}$;
n is 0;
$R^N$ is H;
L is C(=O);
Q is Q1, wherein $B^3$ is X—$R^X$.

Accordingly, the compound is a compound of formula (X):

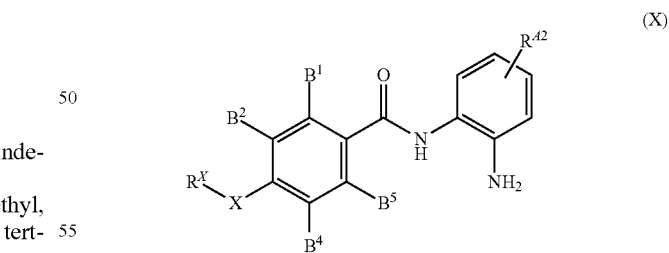

(X)

wherein X, $R^X$, $B^1$, $B^2$, $B^4$, $B^5$ and $R^{A2}$ are as previously defined.

In some embodiments:
$A^1$ and $A^2$, together with the atoms to which they are bound, form a phenyl ring;
n is 0;
$R^N$ is H;
L is C(=O);
Q is Q1, wherein $B^3$ is X—$R^X$ and $B^1$, $B^2$, $B^4$ and $B^5$ are all H.

Accordingly, the compound is a compound of formula (XI):

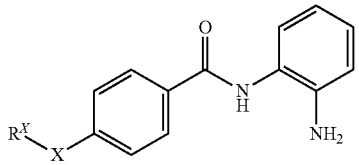

(XI)

wherein X and $R^X$ are as previously defined.

In some embodiments:
$A^1$ and $A^2$, together with the atoms to which they are bound, form a phenyl ring;
n is 0;
$R^N$ is H;
Q is Q1.

Accordingly, the compound is a compound of formula (XII):

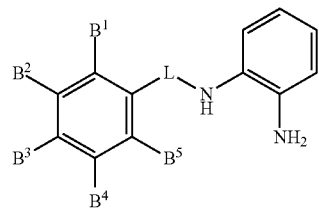

(XII)

wherein $B^1$, $B^2$, $B^3$, $B^4$, $B^5$ and L are as previously defined.

In some embodiments:
$A^1$ and $A^2$, together with the atoms to which they are bound, form a phenyl ring;
n is 0;
$R^N$ is H;
Q is Q1, wherein $B^3$ is X—$R^X$ and $B^1$, $B^2$, $B^4$ and $B^5$ are all H.

Accordingly, the compound is a compound of formula (XIII):

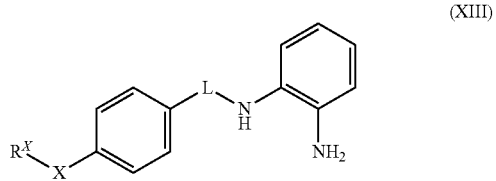

(XIII)

wherein X, $R^X$, and L are as previously defined.

Specific Compounds

In some embodiments, the compound is selected from:

| # | Name | Structure |
|---|------|-----------|
| 1 | N-(2-Aminophenyl)benzamide | 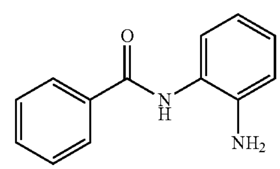 [SMILES: Nc1ccccc1NC(=O)c1ccccc1] |
| 2 | N-(2-Aminophenyl)-4-methoxybenzamide | 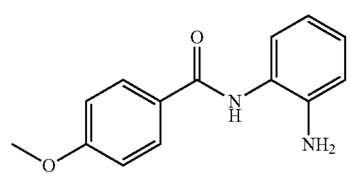 [SMILES: COc1ccc(C(=O)Nc2ccccc2N)cc1] |
| 3 | N-(2-Aminophenyl)-4-nitrobenzamide | 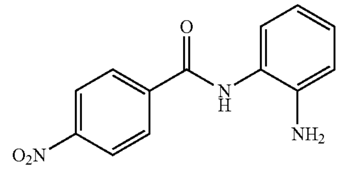 [SMILES: Nc1ccccc1NC(=O)c1ccc([N+](=O)[O-])cc1] |

-continued

| # | Name | Structure |
|---|------|-----------|
| 4 | Benzyl (4-((2-aminophenyl)carbamoyl)-benzyl)carbamate | 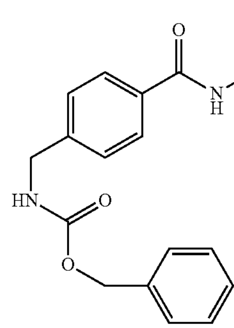 |
| 5 | Pyridin-3-ylmethyl (4-((2-aminophenyl)-carbamoyl)benzyl)carbamate (Entinostat) | 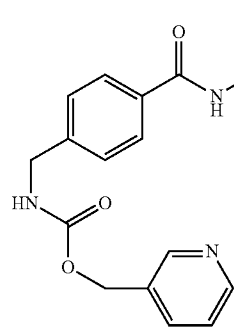 |
| 6 | Methyl 2-(4-((4-((2-aminophenyl) carbamoyl)benzyl)carbamoyl)-1H-1,2,3-triazol-1-yl)acetate (6b = acetate salt) | 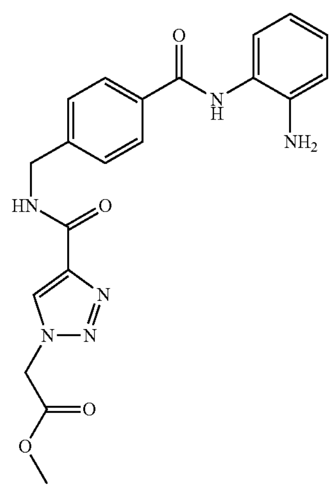 [SMILES: COC(=O)Cn1cc(C(=O)NCc2ccc(C(=O)Nc3ccccc3N)cc2)nn1] |
| 7 | $N^1$-(2-aminophenyl)-$N^4$-(4-(dimethylamino)phenyl)terephthalamide | 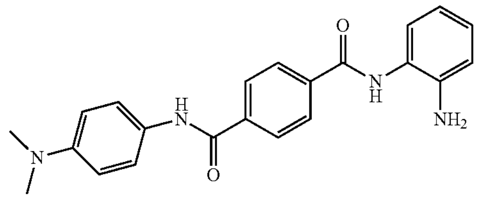 [SMILES: CN(C)c1ccc(NC(=O)c2ccc(C(=O)Nc3ccccc3N)cc2)cc1] |
| 8 | $N^1,N^4$-bis(2-aminophenyl)terephthalamide | 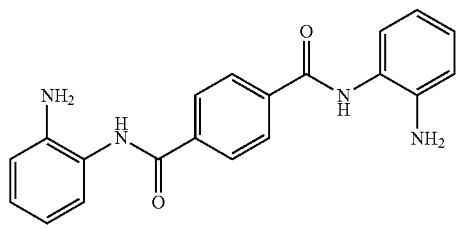 [SMILES: Nc1ccccc1NC(=O)c1ccc(C(=O)Nc2ccccc2N)cc1] |

-continued

| # | Name | Structure |
|---|------|-----------|
| 9 | $N^1$-(2-aminophenyl)-$N^5$-(4-(dimethylamino)-phenyl)glutaramide | 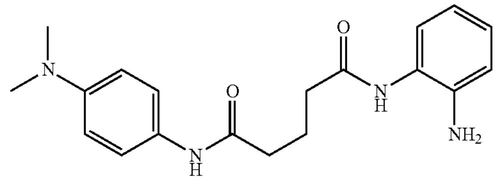 [SMILES: CN(C)c1ccc(NC(=O)CCCC(=O)Nc2ccccc2N)cc1] |
| 10 | (9 H-fluoren-9-yl)methyl (4-((2-aminophenyl) carbamoyl)-benzyl)carbamate | 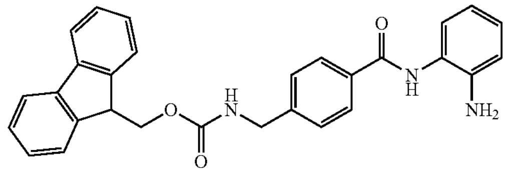 [SMILES: Nc1ccccc1NC(=O)c1ccc(CNC(=O)OCC2c3ccccc3-c3ccccc32)cc1] |

The compounds described herein may thus be used in the treatment and or prevention of infections, alone or as adjunctive therapy.

Compounds described herein may be novel per se. Thus aspects of the invention extend to those compounds per se, in addition to their uses in the therapeutic methods described herein.

The term "treatment," as used herein in the context of treating a disorder, pertains generally to treatment and therapy, whether of a human or another animal (e.g. mammal), in which some desired therapeutic effect is achieved, for example, the inhibition of the progress of the disorder, and includes a reduction in the rate of progress, a halt in the rate of progress, alleviation of symptoms of the disorder, amelioration of the disorder, and cure of the disorder. The methods and compositions of the present invention will be understood to have utility in aquaculture, veterinary and animal husbandry applications for companion animals, farm animals, and ranch animals. These applications include but are not limited to treating, preventing or counteracting microbial diseases and conditions in fish, dogs, cats, cows, horses, deer and poultry including hen, turkey ducks, geese; as well as in household pets such as birds and rodents. For large animals, a suitable dose can be larger than the above mentioned amounts.

Treatment as a prophylactic measure (i.e., prophylaxis) is also included. For example, use with patients who have not yet developed the disorder, but who are at risk of developing the disorder, is encompassed by the term "treatment." "Prophylaxis" in the context of the present specification should not be understood to circumscribe complete success i.e. complete protection or complete prevention. Rather prophylaxis in the present context refers to a measure which is administered in advance of detection of a symptomatic condition with the aim of preserving health by helping to delay, mitigate or avoid that particular condition.

The gastrointestinal tract (GI tract) of mammals is covered by a continuous sheet of epithelial cells that is folded into villus projections and crypts. Within the base of the crypts, where the stem cells of the GI tract can be found, there are specialized, granular cells called Paneth cells. Both enterocytes and Paneth cells produce antimicrobial peptides. The enterocytes synthesize and secrete antimicrobial peptides into the gut lumen both constitutively and upon induction. The Paneth cells at the base of the intestinal crypts, secrete alpha-defensins into the cryptal well, resulting in concentrations estimated at mg/mL levels, which eventually flush into the gut lumen. Additionally stationary macrophages are also known to secrete antimicrobial peptides into the gut lumen and additional tissue sites when activated.

Both systems contribute to bowel health. In children and adults suffering from diarrhoea caused by *Shigella*, synthesis of the cathelicidin LL-37 and the colonic enterocyte beta-defensin HBD-1 is markedly supressed; expression recovers in time during resolution of the illness. Similarly, mice which lack the proteolytic enzyme required for processing cryptdins (the murine Paneth cell alpha-defensins) lack functional cryptdins and exhibit increased susceptibility to orally administered *Salmonella*.

Other epithelial surfaces of the mammalian body also have such host defense secretion systems, including but not limited to the cornea, the lung, the kidney and the skin (see also WO2012/140504).

The use of the compositions and methods of the present invention will result in the stimulation of macrophages and epithelial cells and Paneth cells of the gastrointestinal tract and other epithelial surfaces of man and in other animals to secrete large quantities of naturally occurring broad-spectrum antimicrobial agents, including antimicrobial peptides such as defensins, HMP 1-4, LL-37, HBD1-4, and antimicrobial proteins such as lysozyme, transferrin, lactoferrin, phospholipases, and SLPI (secretory leukocyte protease inhibitor). The substances stored by the Paneth cells exhibit activity against a wide range of infectious agents including bacteria, protozoa, viruses, and fungi.

The epithelial cells targeted by the present invention may be any of these e.g. in the lung, trachea, urinary tract or kidney, upper GI tract (e.g. ileum) and lower GI tract (e.g. jejunum) and\or blood. Preferably however the invention is utilised for the treatment of microbial infections of the GI tract.

As mentioned, an important aspect of the invention provides methods for treating, preventing or counteracting microbial infections e.g. by administering a medicament comprising a secretagogue-effective amount of at least one compound of the invention.

In useful embodiments, infections and other conditions that benefit from treatment according to the invention are in particular those relating to organs having epithelial surfaces with host defense peptide secretion systems such as the above mentioned.

The compounds of the invention are particularly useful against infections of bacterial strains that are tolerant against conventional antibiotics. Bacterial species include, but are not limited to *Yersenia, Salmonella, Shigella, Campylobacter, Clostridium, Heliobacter, Mycobacterium, Pseudomonas, Haemophilus, Moraxella, Escherichia, Neisseria* and *Staphyllococcus* strains. Also embraced is the targeting of viruses, including HIV, RSV, herpes, hepatitis and influenza viruses, which are also believed to be a target for the antimicrobial peptides stimulated by the present invention.

Infections, conditions and diseases treatable according to the present invention include, but are not limited to:

Shigellosis; traveller's diarrhoea, endemic diarrhoea, dysentery, viral gastroenteritis, parasitic enteritis, Crohn's disease, ulcerative colitis, irritable bowel syndrome, precancerous states of the gastrointestinal tract, cancer of the gastrointestinal tract, diverticulitis, post-antibiotic diarrhoea, *Clostridium difficile* colitis, lactose intolerance, flatulence, gastritis, esophagitis, heartburn, gastric ulcer, ulcers associated with *Helicobacter pylori*, duodenal ulcer, short bowel syndrome, dumping syndrome, gluten enteropathy;

Eye infections optionally selected from conjunctivitis, stye, blepharitis, cellulitis of the eye, keratitis, corneal ulcer, trachoma, uveitis, canaliculitis and dacryocystitis;

Urinary tract and genital infections optionally selected from pyelonephritis, cystitis, gonorrhoea and urethritis;

Infections of the respiratory system optionally selected from bronchitis, pneumonia, rhinosinusitis, sinusitis, pharyngitis/tonsillitis, laryngitis and influenza; tuberculosis;

Skin infections optionally selected from boils, carbuncles, furuncles, cellulitis, abscesses, impetigo, and erysipelas;

The term "treatment" includes combination treatments and therapies, in which two or more treatments or therapies are combined, for example, sequentially or simultaneously.

The agents (i.e. the compound described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g. 1, 2, 3, 4 or more hours apart, or even longer periods apart where required), the precise dosage regimen being commensurate with the properties of the therapeutic agent(s) as described herein, including their synergistic effect.

The agents (i.e. the compound described here, plus one or more other agents) may be formulated together in a single dosage form, or alternatively, the individual agents may be formulated separately and presented together in the form of a kit, optionally with instructions for their use.

For example, the compounds described herein may in any aspect and embodiment also be used in combination therapies, e.g. in conjunction with other agents. Such agents may be as follows:

Butyrate and PBA

Sodium phenylbutyrate is a known medicament. For example it has been marketed by Ucyclyd Pharma (Hunt Valley, USA) under the trade name Buphenyl and by Swedish Orphan Biovitrum AB (Sweden) as Ammonaps. It has been used to treat urea cycle disorders (Batshaw et al. (2001) *J. Pediatr.* 138 (1 Suppl): S46-54; discussion S54-5). Scandinavian Formulas, Inc. Sellersville, Pa. supplies sodium phenylbutyrate worldwide for clinical trials. Sodium phenylbutyrate is also under investigation for the treatment of some sickle-cell disorders (Blood Products Plasma Expanders and Haemostatics) and for use as a potential differentiation-inducing agent in malignant glioma and acute myeloid leukaemia. It has also been investigated in respect of cystic fibrosis pathology due to its capacity to traffic DeltaF508-cystic fibrosis transmembrane conductance regulator (CFTR) to the cell membrane and restore CFTR chloride function at the plasma membrane of CF lung cells in vitro and in vivo (Roque et al. J Pharmacol Exp Ther. 2008 September; 326(3):949-56. Epub 2008 Jun. 23). It is believed in the literature that phenylbutyrate is a prodrug which is metabolized in the body by beta-oxidation to phenylacetate.

Vitamin D

The new class of compounds works synergistically with vitamin D as shown with pyridin-3-ylmethyl (4-((2-aminophenyl)carbamoyl)benzyl)carbamate. Vitamin D type compounds are discussed in US20080038374 or WO/2008/073174. Where the term "Vitamin D" is used herein, it is used in a broad sense to encompass Vitamin D3 (or "1,25 D3") and its hormonally active forms, to include compounds which are structurally similar to vitamin D3. Many of these compounds are recognized and comprise a large number of natural precursors, metabolites, as well as synthetic analogs of the hormonally active 1, 25-dihydroxyvitamin D3 (1α25 $(OH)_2$D3). This language is intended to include vitamin D3, or an analog thereof, at any stage of its metabolism, as well as mixtures of different metabolic forms of vitamin D3 or analogs thereof.

Antibiotics

The compounds of the invention are particularly useful against infections of bacterial strains that are tolerant against conventional antibiotics. Nevertheless use of the compounds described herein in conjunction with conventional antibiotics may be preferred and forms one part of the present invention.

Example antibiotics include Penicillins, Penicillin G, Phenoxymethyl-penicillin, Flucloxacillin, Amoxycillin, Metronidazole, Cefuroxime, Augmentin, Pivmecillinam, Acetomycin, Ciprofloxacin and Erythromycin. Where these specific antibiotics are named, it will be appreciated that commonly available analogs may be used.

As noted above, in certain aspects, it may be preferred to use the compounds described herein in conjunction with a known antibiotic, as follows:

(1) acute administration to the patient of an antibiotic for preferably 1, or 2, days with or without a compound of formula (I); followed by, (2) administration to the patient of an effective amount of a compound of formula (I) for a further 2, 3, 4, 5 or more days.

Such a regime may have benefits in minimising the development of antibiotic resistance in the pathogen to be targeted.

Isoleucine and Related Compounds

The amino acid L-isoleucine upregulates β-defensins expression in epithelial cells of cows (18). US2002-0076393 (Fehlbaum et al.); US2003-0109582 (Zasloff); U.S. Pat. No. 7,311,925 (Zasloff) also relate to the use of isoleucine, an active isomer thereof, and an active analog thereof, in each case for stimulation of the innate antimicrobial defence system.

The disclosure of all these references, in respect of these compounds, their definition, and their provision, is hereby specifically incorporated herein by cross-reference.

Also provided are pharmaceutical compositions comprising, in addition to one or more of the compounds of the invention, vitamin D or one of the other aforementioned compounds as a further ingredient. Such compositions can be formulated in any of the above mentioned formulations and dosage forms.

Oral or inhalation dosage forms are preferred, as described below.

Dosages

In particular aspects of the invention there are provided methods for treating, preventing or counteracting a microbial infection in a patient in need of the same, by administering to the patient an effective amount of a compound of the invention as described herein.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

The compounds of the present invention exhibit an antimicrobial effect by stimulating the innate antimicrobial peptide defense system and\or stimulating autophagy.

Thus an effective amount in the present context would be one which is sufficient to demonstrate antimicrobial activity in vivo e.g. by stimulating (e.g. supressing or counteracting down-regulation caused by several pathogens) synthesis of the cathelicidin LL-37 or other naturally occurring antibiotic peptide or protein e.g. a defensin. Stimulation may be towards, equal to, or above basal levels (i.e. normal levels in the absence of the infection). Preferred compounds of the present invention are believed to be more stable, and have a longer half-life, than stimulatory compounds used in the prior art, such as PBA.

By the term "antimicrobial activity" as used herein, is meant the ability to inhibit the growth of or actually kill a population of microbes which can be bacteria, viruses, protozoa or fungal microbes. Thus "antimicrobial activity" should be construed to mean both microbistatic as well as microbicidal activities. Antimicrobial activity should also be construed to include a compound which is capable of inhibiting infections, i.e. disease-causing capacity of microbes. Generally the use of the present invention will be such as to lead to secretion of the relevant peptide onto an epithelial surface.

Preferred dosages and dosage forms are described in more detail below.

A preferred dosage of a compound of type I (e.g. Compound 5) may be: between 25 μg and 2000 mg; more preferably 0.05 mg to 500 mg; more preferably 0.1 to 250 mg; more preferably about 0.2 to 100 mg; more preferably less than or equal to about 50 mg/day In each case dosages can be split into 1, 2, 3, 4, 5, 6 or 7 doses per week or 1, 2 or 3 doses per day. For example 1, 2 or 3×3, 5 or 10 mg/week, 1 or 2×5 or 50 mg/day or 2×250 mg/week and so on. A preferred regime is less than 3× per day e.g. 1 or 3×3 mg/week, 2×1 mg/day or 2×5 mg/week.

A preferred dosage may be between 0.1 mg and 100 mg; between 0.2 mg and 50 mg; between 0.2 mg and 20 mg; optionally with vitamin D3.

Thus preferred dosages can be split into 1, 2, 3, or 4 doses per week or 1, 2 doses per day. For example 1 or 3×2 mg/week, 2×0.5 mg/day and so on.

Corresponding preferred weight\molar amounts for other compounds of the invention can be calculated by those skilled in the art based on the disclosure herein.

Dosages for Vitamin D may be of the order of 1000-10 000 IU daily.

Dosage Forms

The compound of the invention is preferably administered in an oral dosage form such as, but not limited to, a tablet, a capsule, a solution, a suspension, a powder, a paste, an elixir, and a syrup.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and antioxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Other administration forms are also useful, these include but not are limited to topical administration forms, which are in particular useful against infections of the skin, these include for example creams, oils, lotions, and ointments. Yet further dosage forms include dosage forms for delivery to the respiratory system including the lungs, such as aerosols and nasal spray devices or by rectal enema.

Definitions

The term 'alkyl', as used herein, refers to a monovalent moiety obtained by removing a hydrogen atom from a saturated aliphatic hydrocarbon compound, preferably having from 1 to 4 carbon atoms ('$C_{1-4}$alkyl'), which may be linear or branched.

Examples of $C_{1-4}$ alkyl groups include, but are not limited to, methyl, ethyl, n-propyl, iso-propyl, n-butyl, iso-butyl, sec-butyl, tert-butyl. In certain instances, methyl or ethyl groups may be preferred.

Similarly, the term 'alkylene' refers to a divalent moiety obtained by removing two hydrogen atoms from a saturated aliphatic hydrocarbon compound, preferably having from 1 to 3 carbon atoms ('$C_{1-3}$alkylene'), which may be linear or branched.

Examples of $C_{1-3}$alkylene groups include, but are not limited to, —$CH_2$—, —$CH_2CH_2$—, —$CH_2CH_2CH_2$—, —$CH(CH_3)$—, —$CH(CH_3)CH_2$—, —$CH_2CH(CH_3)$—, or —$CH(CH_2CH_3)$—.

The term 'cycloalkyl', as used herein, refers to a monovalent moiety obtained by removing a hydrogen atom from a saturated alicyclic hydrocarbon compound, preferably having from 3 to 6 ring atoms ('$C_{3-6}$cycloalkyl').

Examples of $C_{3-6}$cycloalkyl groups include, but are not limited to, cyclopropyl, cyclobutyl, cyclopentyl, and cyclohexyl, as well as substituted groups (e.g., groups which comprise such groups), such as methylcyclopropyl, dimethylcyclopropyl, methylcyclobutyl, dimethylcyclobutyl, methylcyclopentyl, dimethylcyclopentyl, methylcyclohexyl, dimethylcyclohexyl, cyclopropylmethyl and cyclohexylmethyl.

The term "$C_{6-14}$ aryl", as used herein, pertains to a monovalent moiety obtained by removing a hydrogen atom from an aromatic ring atom of a $C_{6-14}$ aromatic compound, said compound having one ring, or two or more rings (e.g., fused), and having from 6 to 14 ring atoms, and wherein at least one of said ring(s) is an aromatic ring. Preferably, each ring has from 6 to 10 ring atoms. The term "$C_{6-14}$ aromatic ring" may also be used and should be construed accordingly; this may refer to a multivalent moiety.

The ring atoms may be all carbon atoms, as in "carboaryl groups", in which case the group may conveniently be referred to as a "$C_{6-14}$ carboaryl" group.

Examples of $C_{6-14}$carboaryl groups include, but are not limited to, those derived from benzene (i.e. phenyl) ($C_6$), naphthalene ($C_{10}$), anthracene ($C_{14}$), and phenanthrene ($C_{14}$).

Examples of aryl groups which comprise fused rings, one of which is not an aromatic ring, include, but are not limited to, groups derived from indene and fluorene, e.g.:

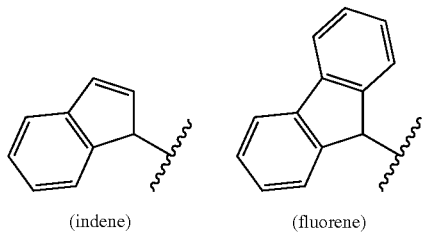 [SMILES: *C1C=Cc2ccccc21 ; *C1c2ccccc2-c2ccccc21]

(indene)    (fluorene)

The term 'heteroaryl', as used herein, refers to a monovalent moiety obtained by removing a hydrogen atom from an aromatic ring atom of a heteroaromatic compound, i.e. a compound containing at least one aromatic ring, wherein the ring atoms include at least one heteroatom. Possible heteroatoms include but are not limited to oxygen, nitrogen, and sulphur. Preferably, the aromatic ring has from 5 to 6 ring atoms, of which from 0 to 4 are ring heteroatoms. In this case, the group is referred to as a '$C_{5-6}$heteroaryl' group, wherein '$C_{5-6}$' denotes ring atoms whether carbon atoms or heteroatoms.

Examples of $C_{5-6}$heteroaryl group include, but are not limited to, $C_5$ heteroaryl groups derived from furan (oxole), thiophene (thiole), pyrrole (azole), imidazole (1,3-diazole), pyrazole (1,2-diazole), triazole (1,2,3-triazole, 1,2,4-triazole), oxazole, isoxazole, thiazole, isothiazole, oxadiazole, and oxatriazole; and $C_6$ heteroaryl groups derived from isoxazine, pyridine (azine), pyridazine (1,2-diazine), pyrimidine (1,3-diazine; e.g., cytosine, thymine, uracil), pyrazine (1,4-diazine), triazine, tetrazole, and oxadiazole (furazan).

The term 'halo' or 'halogen' refers to —F, —Cl, —Br, and —I substituents. Fluoro (—F) and chloro (—Cl) substituents are usually preferred.

Isomers, Salts, Solvates, and Protected Forms

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

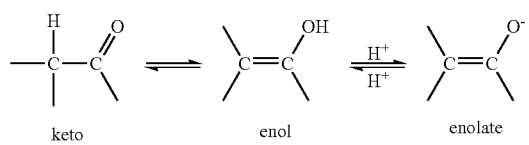

keto    enol    enolate

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g. asymmetric synthesis) and separation (e.g., fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge, et al., J. Pharm. Sci., 66, 1-19 (1977).

For example, if the compound is anionic, or has a functional group which may be anionic (e.g., —COOH may be —COO$^−$), then a salt may be formed with a suitable cation. Examples of suitable inorganic cations include, but are not limited to, alkali metal ions such as Na$^+$ and K$^+$, alkaline earth cations such as Ca$^+$ and Mg$^+$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulphuric, sulphurous, nitric, nitrous, phosphoric, and phosphorous. Examples of suitable organic anions include, but are not limited to, those derived from the following organic acids: acetic, propionic, succinic, glycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetyoxybenzoic, fumaric, phenylsulfonic, toluenesulfonic, methanesulfonic, ethanesulfonic, ethane disulfonic, oxalic, pantothenic, isethionic, valeric, lactobionic, and gluconic. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form", as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, Protective Groups in Organic Synthesis (T. Green and P. Wuts, Wiley, 1999).

For example, a hydroxy group may be protected as an ether (—OR) or an ester (—OC(═O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(═O)CH$_3$, —OAc).

For example, an aldehyde or ketone group may be protected as an acetal or ketal, respectively, in which the carbonyl group (>C═O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide or a urethane, for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH—Fmoc), as a 6-nitroveratryloxy amide (—NH—Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH—Psec); or, in suitable cases, as an N-oxide (>NO.).

For example, a carboxylic acid group may be protected as an ester for example, as: an C$_{1-7}$ alkyl ester (e.g. a methyl ester; a t-butyl ester); a C$_{1-7}$ haloalkyl ester (e.g., a C$_{1-7}$ trihaloalkyl ester); a triC$_{1-7}$ alkylsilyl-C$_{1-7}$ alkyl ester; or a C$_{5-20}$ aryl-C$_{1-7}$ alkyl ester (e.g. a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(═O)CH$_3$).

Any sub-titles herein are included for convenience only, and are not to be construed as limiting the disclosure in any way.

The invention will now be further described with reference to the following non-limiting Figures and Examples. Other embodiments of the invention will occur to those skilled in the art in the light of these.

The disclosure of all references cited herein, in as much as it may be used by those skilled in the art to carry out the invention, is hereby specifically incorporated herein by cross-reference.

FIGURES

FIG. 1. Structures of compounds representing the new class of inducers of antimicrobial peptides (structures 1-10 and 16) as well as of the known inducer PBA (13) and reference control substances (structures 11, 12, 14, 15 and 17-19).

Figure 2:
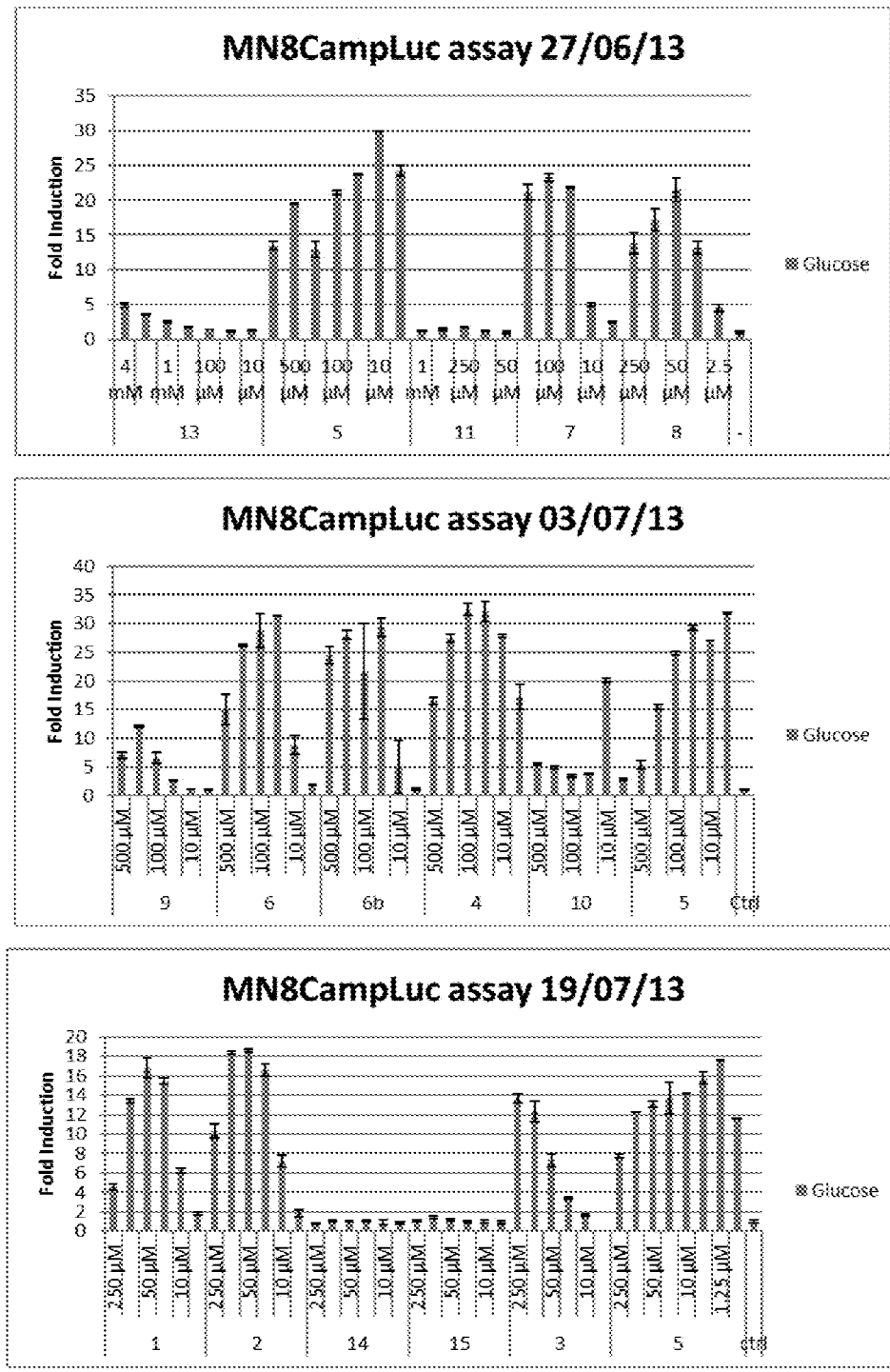

FIG. 2. Fold induction assays in the MN8CampLuc reporter cell line with compounds 1-11 and 13-15.

Figure 3:
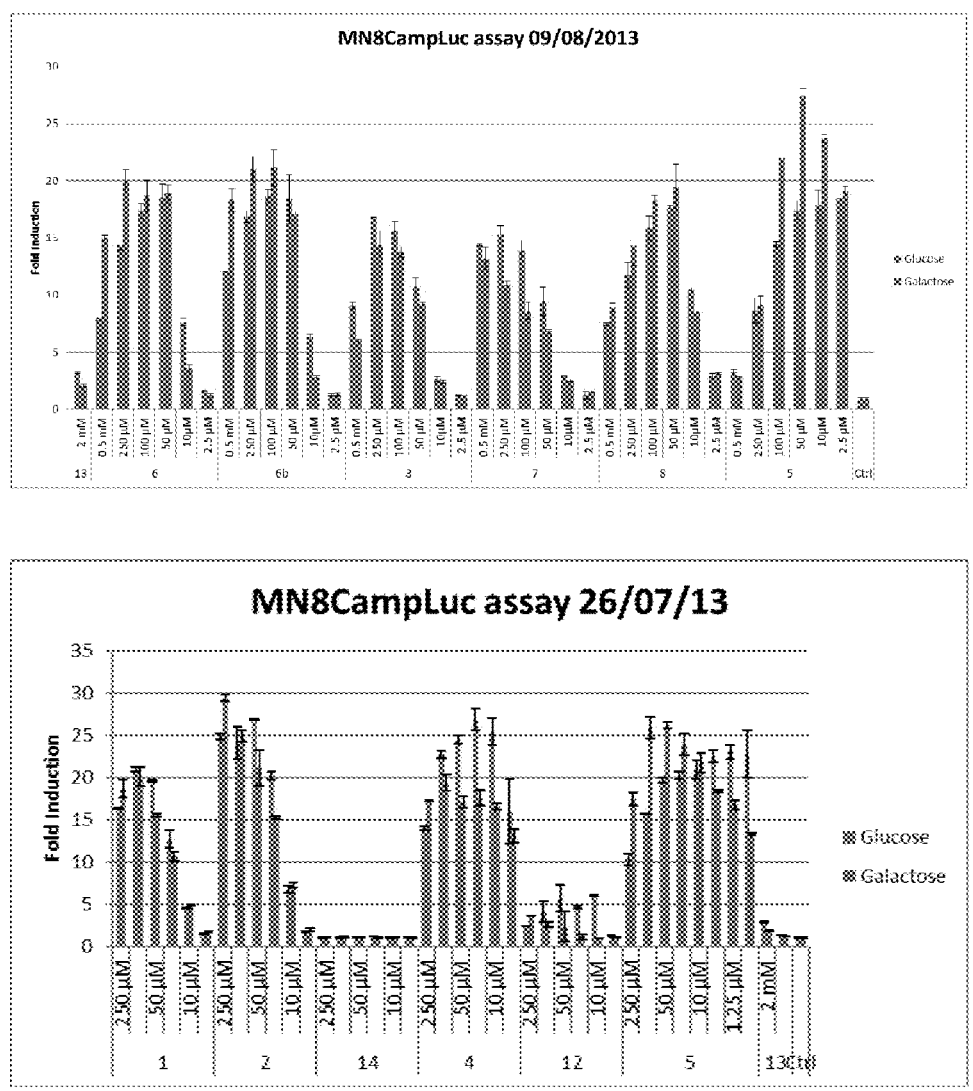

FIG. 3. Comparative fold induction assays in the MN8CampLuc reporter cell line (32) with and without pre-differentiation of cells by treatment with galactose.

Figure 4:
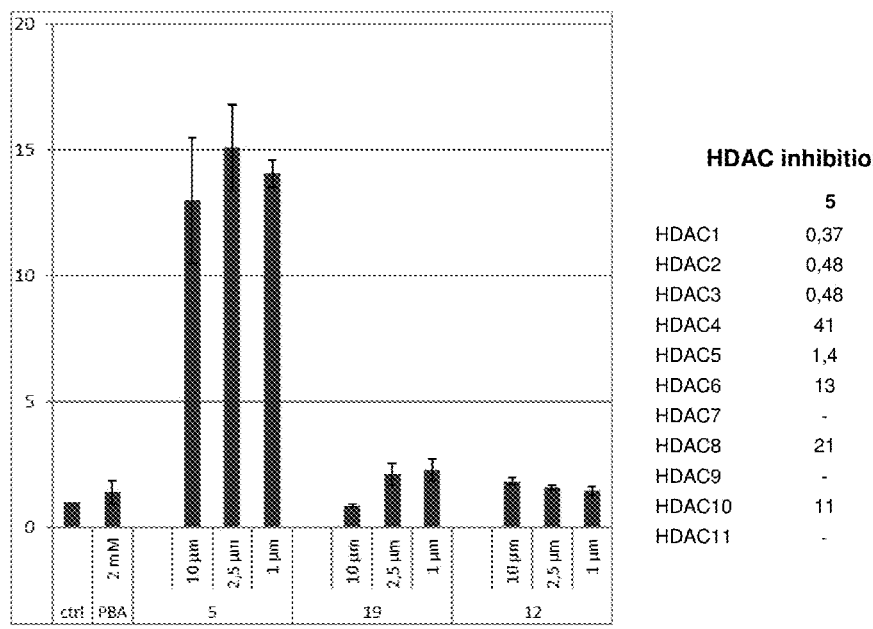

FIG. 4. Left panel: Fold induction (as luciferase activity) assays in the MN8CampLuc reporter cell line with compound 5 compared to treatment with the known HDAC inhibitors Trichostatin A (19) and Vorinostat (12) (data was obtained from cells that were pre-differentiated by treatment with galactose). Right panel: Table with IC$_{50}$ values for HDAC inhibition of different histone deacetylases by compounds 5, 12 and 19. The average IC$_{50}$ values from all reported assays in PubChem (2014 Apr. 12) was used. Assays with any data from specific compounds deviating more than 2 standard deviations from the average, were excluded.

Figure 5:
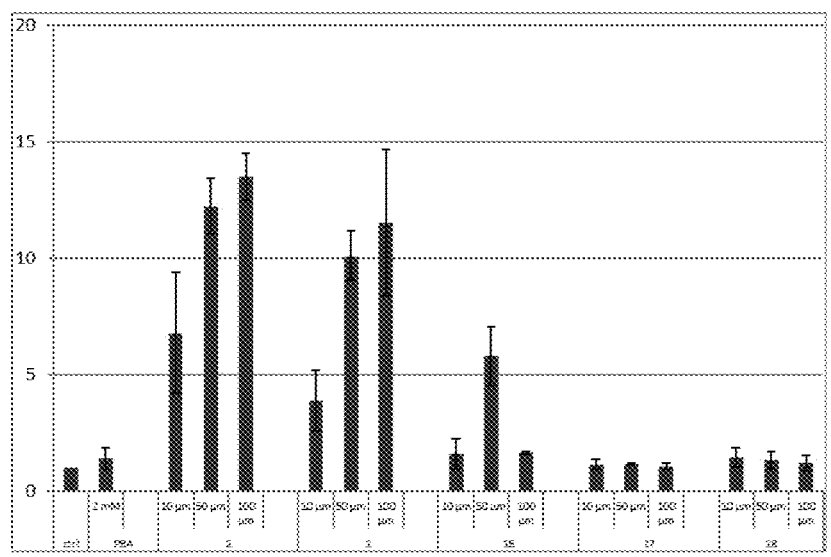

FIG. 5. Fold induction (as luciferase activity) assays in the MN8CampLuc reporter cell line with compounds 1 and 2 compared to treatment with structurally similar compounds 16-18 (data was obtained from cells that were pre-differentiated by treatment with galactose).

Figure 6:
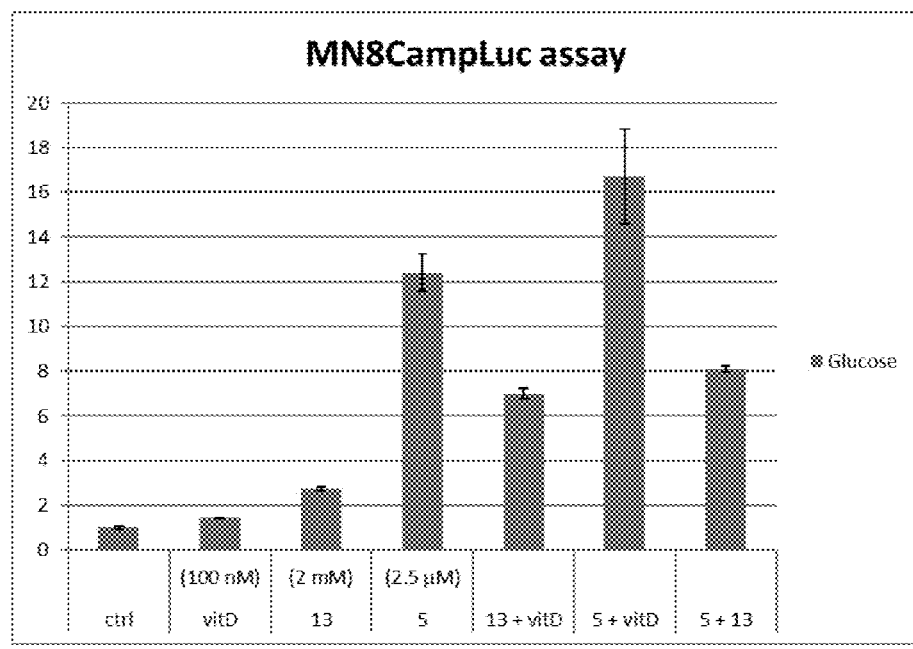

FIG. 6. Further testing of pyridin-3-ylmethyl (4-((2-aminophenyl)carbamoyl)benzyl)-carbamate (5) and PBA (13) in the reporter cell line in combination with VitD.

Figure 7:
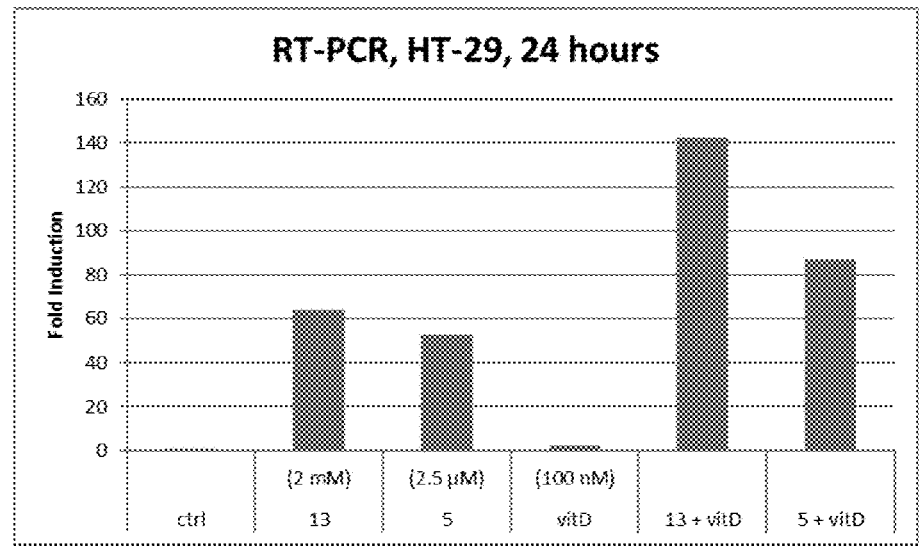

FIG. 7. Pyridin-3-ylmethyl (4-((2-aminophenyl)carbamoyl)benzyl)carbamate (5) and PBA (13) induction of the CAMP gene in the parental HT-29 cell line and also in combination with VitD.

Figure 8:
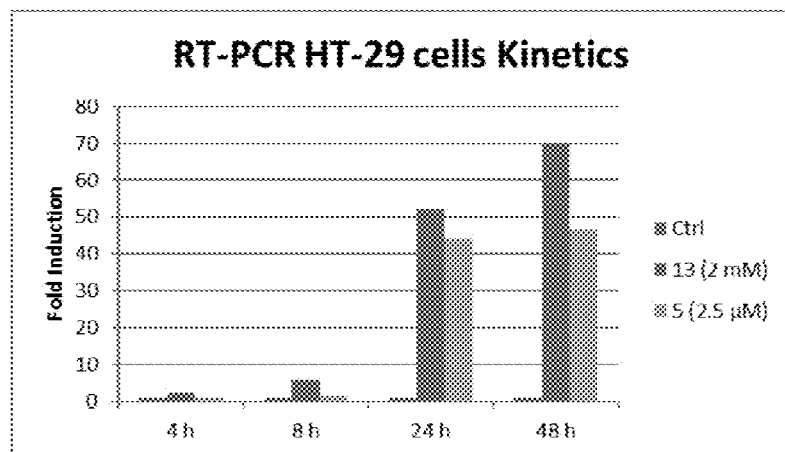

FIG. 8. RT-PCR on the parental HT29 cell line at different times after treatment with PBA (13) and pyridin-3-ylmethyl (4-((2-aminophenyl)carbamoyl)benzyl)carbamate (5).

Figure 9:
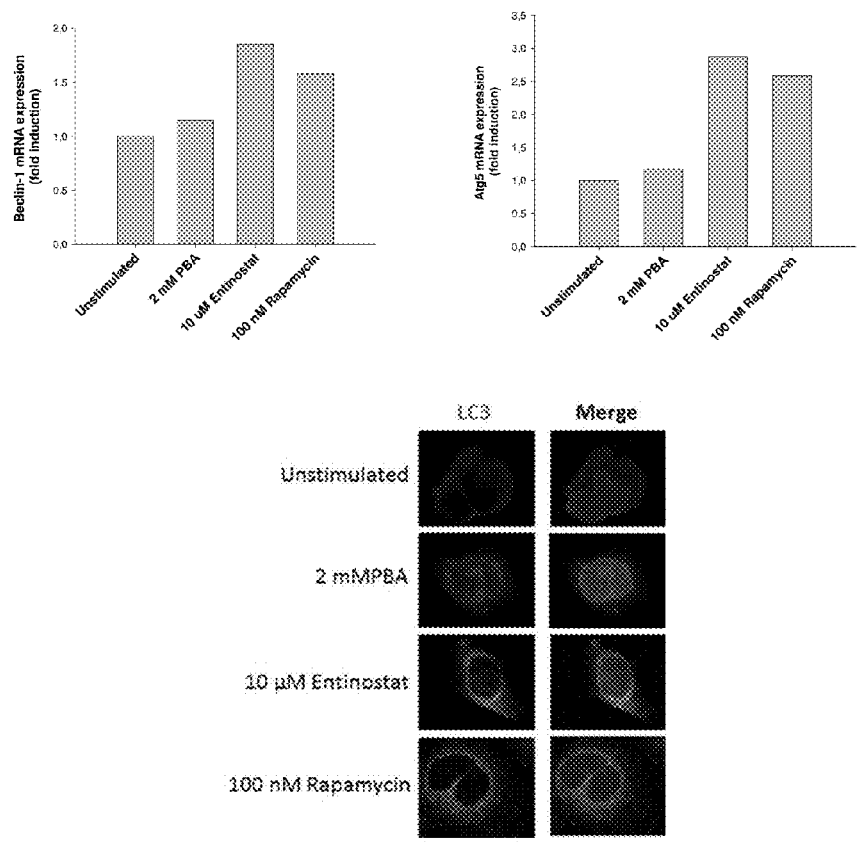

FIG. 9. Upper panel: RT-PCR showing increased expression of autophagy-related genes Beclin-1 and AtgS in HEK-293 cells treated with PBA (2 mM), compound 5 (Entinostat, 10 μM) and Rapamycin (100 nM) (positive control) for 24 hrs. Lower panel: Fluorescence spectroscopy of HEK-293 cells treated with PBA (2 mM), compound 5 (10 μM) and Rapamycin (100 nM) for 24 hrs.

EXAMPLES

Methods and Materials

MN8CampLuc cells were handled according to Nylen et. al. with the following exception when predifferention of cells were performed before induction:

Cell seeding was performed in medium where glucose was exchanged for galactose (5 mg/ml), which is known to promote differentiation in colon epithelial cells (Pinto, M., M. D. Appay, P. Simon-Assman, G. Chevalier, N. Dracopoli, J. Fogh, and A. Zweibaum, 1982, Biol. Cell., 44:193-196) Cells were then allowed to grow for 72 hours before stimulation with test compounds.

RT-PCR experiments were performed according to Nylen et. al. (Nylén F, Miraglia E, Cederlund A, Ottosson H, Stromberg R, Gudmundsson G H, Agerberth B. 2013. Boosting innate immunity: Development and validation of a cell-based screening assay to identify LL-37 inducers. Innate Immun.).

RT-PCR experiments for expression of marker genes for autophagy in HEK-293 cells were measured by real-time PCR. Data were normalized by the expression of the 18s rRNA housekeeping gene. For the immunofluorescence spectroscopy experiments HEK-293 cells were fixed after treatment with the inducers or control. The cells were then stained with DAPI to visualize the nuclei (blue), and immunolabeled with the anti-LC3, followed by the addition of Alexa-fluor 488 (green). Scale bar=10 μm.

All reagents and solvents (analytical grade) were purchased from commercial resources and were used without further purification. The NMR spectra were collected on a Bruker DRX-400 spectrometer (400 MHz for $^1$H and 101 MHz for $^{13}$C) with the residual solvent signal as chemical shift reference. Mass spectra were recorded on a Micromass LCT (ESI-TOF) mass spectrometer. Pyridin-3-ylmethyl (4-((2-aminophenyl)carbamoyl)benzyl)carbamate (5, Entinostat) and N1-hydroxy-N8-phenyloctanediamide (12, Vorinostat) was purchased from LC laboratories (Woburn, Mass., USA), N-(4-Methoxybenzyl)-1,2-benzenediamine (16) from Fluorochem Ltd (Hadfield, UK) and Trichostatin A (19) from Sigma-Aldrich Sweden AB (Stockholm, Sweden).

Example 1. Synthesis of N-(2-Aminophenyl)benzamide (1)

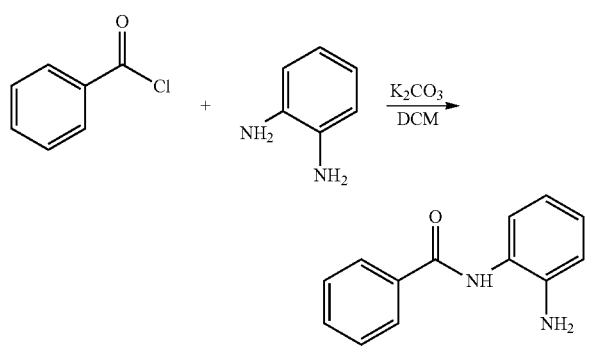

To a solution of 1,2-phenylenediamine (1.8 g, 16.6 mmol) in dichloromethane (40 mL) at room temperature was added potassium carbonate (1.28 g, 9.26 mmol) and benzoyl chloride (1.00 mL, 8.62 mmol). After about 30 s a precipitate was formed. The mixture was stirred for 1 hr, the precipitate was filtered off and washed with dichloromethane. The filtrate was washed with water and then extracted with HCl (1 M). Some precipitate was formed while extracting, this was filtered off. The water layer was basified with NaOH (aq) and extracted with dichloromethane. The dichloromethane layer was dried with sodium sulfate and evaporated. The resulting solid was recrystallized from diethyl ether. Several recrystallizations yielded a pure sample (423 mg, 1.99 mmol, 23%). $^1$H NMR (400 MHz, chloroform-d) δ ppm 3.79 (br. s., 1H) 6.74-6.81 (m, 2H) 6.98-7.06 (m, 1H) 7.26 (d, J=8.1 Hz, 1H) 7.38-7.45 (m, 2H) 7.46-7.52 (m, 1H) 7.81 (br. s, 1H) 7.83 (d, J=7.6 Hz, 3H). $^{13}$C NMR (101 MHz, DMSO-$d_6$) δ ppm 118.68, 120.08, 124.86, 125.42, 127.50, 127, 53, 129.04, 132.20, 134, 47, 140.92, 166.08

Example 2. Synthesis of N-(2-Aminophenyl)-4-methoxybenzamide (2)

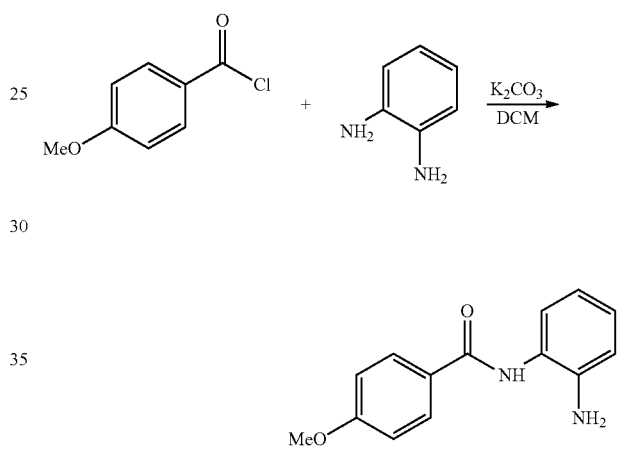

To a solution of 1,2-phenylenediamine (1.3 g, 12 mmol) in dichloromethane (30 mL) at room temperature was added potassium carbonate (1.4 g, 10.0 mmol) and 4-methoxybenzoyl chloride (1.6 g, 9.2 mmol) in dichloromethane (10 mL). The reaction mixture was stirred at room temperature for 1 hr and then diluted with dichloromethane and water to give two clear phases and which was separated. The dichloromethane layer was extracted with HCl (1 M) and a precipitate was formed. This precipitate was filtered off, washed with dichloromethane and some ethanol to give crude product as the hydrochloride salt. The precipitate was recrystallized from ethanol to yield the product as the hydrochloride (310 mg, 1.11 mmol, 12%). The filtrate was washed with water, and then it was extracted with HCl (1 M). This latter water layer was basified with NaOH and extracted with dichloromethane. The dichloromethane layer was dried with sodium sulfate and evaporated to yield crude N-(2-Aminophenyl) 4-methoxybenzamide as the free amine. The resulting solid was recrystallized from ethanol yielded pure product (230 mg, 0.949 mmol, 10%). $^1$H NMR (400 MHz, DMSO-$d_6$) δ ppm 3.85 (s, 3H) 7.07 (d, J=8.8 Hz, 2H) 7.32 (dd, J=8.0, 7.0 Hz, 1H) 7.40 (dd, J=8.0, 7.0 Hz, 1H) 7.50 (d, J=8.1 Hz, 1H) 7.59 (d, J=8.1 Hz, 1H) 8.13 (d, J=8.8 Hz, 2H) 10.45 (s, 1H)$^{13}$C NMR (101 MHz, DMSO-$d_6$) δ ppm 55.50, 113.63, 123.76, 125.68, 126.38, 127.17, 127.22, 127.65, 130.10, 130.10, 131.59, 162.26, 165.21

Example 3. Synthesis of N-(2-Aminophenyl)-4-nitrobenzamide (3)

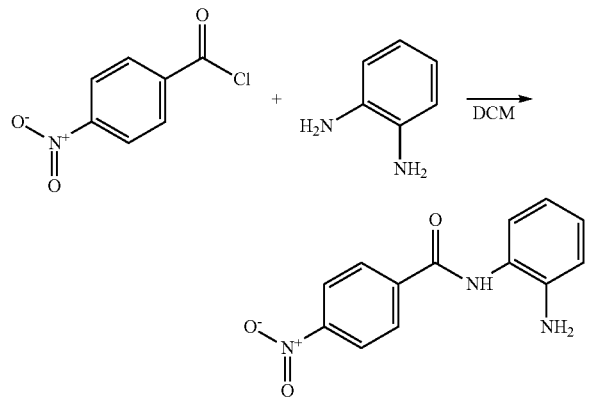

To a solution of 1,2-phenylenediamine (1.86 g, 10.2 mmol) in dichloromethane (100 mL) at room temperature was added p-nitrobenzoyl chloride (2.16 g, 20.0 mmol) and the mixture was stirred overnight. A thick precipitate was formed and was filtered off (contains both mono and dinitrobenzoyl product). The solution was extracted with HCl (1 M). More precipitate was formed and filtered off (mostly mono nitrobenzoyl-product). The water layer was basified with NaOH (ca 5M) and extracted with dichloromethane, washed with water, dried, evaporated. The fractions containing mainly N-(2-Aminophenyl) 4-nitrobenzamide were combined and recrystallization from methanol gave a pure product (67.5 mg pure, 0.262 mmol, 3%). $^1$H NMR (400 MHz, DMSO-d$_6$) δ ppm 4.98 (s, 2H) 6.60 (t, J=7.6 Hz, 1H) 6.79 (d, J=7.6 Hz, 1H) 7.00 (t, J=7.6 Hz, 1H) 7.18 (d, J=7.6 Hz, 1H) 8.22 (d, J=8.6 Hz, 2H) 8.35 (d, J=8.6 Hz, 2H) 9.94 (s, 1H). $^{13}$C NMR (101 MHz, DMSO-d$_6$) δ ppm 115.97, 116.07, 122.48, 123.38, 126.90, 129.30, 140.44, 143.37, 149.04, 163.80

Example 4. Synthesis of Benzyl {4-[(2-aminophenyl)carbamoyl]benzyl}carbamate (4)

a) 4-({[(benzyloxy)carbonyl]amino}methyl)benzoic acid

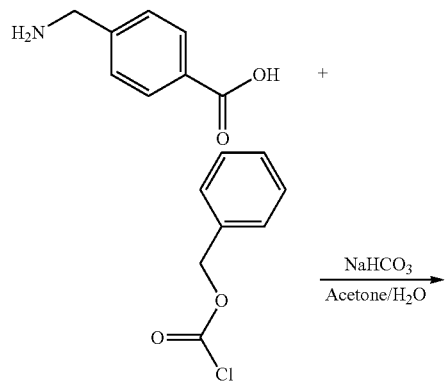

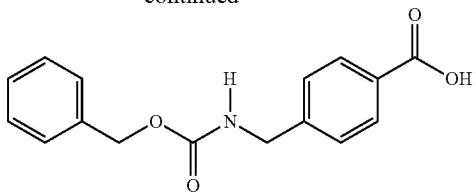

4-(Aminomethyl)benzoic acid (4.53 g, 30.0 mmol) was dissolved in acetone (50 mL), sodium hydrogen carbonate (sat, 50 mL), and water (50 mL). After cooling to 0° C. and an additional adding of ice (ca 10 mL) to the reaction mixture, benzyl chloroformate (4.5 mL, 31.5 mmol) in acetone (25 ml) was added dropwise. The mixture was allowed to attain room temperature and then stirred overnight. The mixture was diluted with water and washed with dichloromethane. The water layer was acidified with HCl (1 M) and extracted with ethyl acetate. The organic layer was basified with NaOH (aq) and a precipitate was formed. This was filtered off, washed with acetone and dichloromethane. Recrystallization from methanol yielded pure product (2.76 g, 9.67 mmol, 32%). $^{13}$C NMR (101 MHz, DMSO-d$_6$) δ ppm 43.77, 65.79, 127.31, 128.01, 128.16, 128.69, 129.45, 129.69, 137.32, 145.24, 156.72, 167.39 b) Benzyl {4-[(2-aminophenyl)carbamoyl]benzyl}carbamate (4)

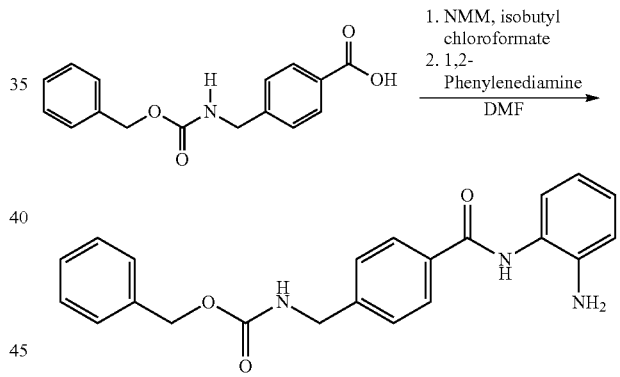

4-({[(benzyloxy)carbonyl]amino}methyl)benzoic acid (313 mg, 1.02 mmol) was evaporated with toluene and then dissolved in DMF (15 ml). N-Methylmorpholine (132 μl 1.20 mmol) was added followed by isobutyl chloroformate (0.17 ml, 1.3 mmol). The mixture was stirred at room temperature for about 15 min whereafter 1,2-phenylendiamine (173 mg, 1.60 mmol) was added. The mixture was stirred at room temperature overnight and then evaporated to yield the crude product as oil. The oil was dissolved in dichloromethane and crystals was formed, filtered off and washed with dichloromethane. Recrystallization from methanol gave pure product (66 mg, 0.176 mmol, 17%)
$^1$H NMR (400 MHz, DMSO-d$_6$) δ ppm 4.29 (d, J=6.1 Hz, 2H) 4.91 (br. s., 2H) 5.06 (s, 2H) 6.61 (t, J=7.6 Hz, 1H) 6.79 (d, J=7.6 Hz, 1H) 6.97 (t, J=7.6 Hz, 1H) 7.18 (d, J=7.6 Hz, 1H) 7.28-7.46 (m, 7H) 7.91 (t, J=5.5 Hz, 1H) 7.94 (d, J=8.1 Hz, 3H) 9.63 (s, 1H) $^{13}$C NMR (101 MHz, DMSO-d$_6$) δ ppm 43.60, 65.46, 116.16, 116.29, 123.37, 126.45, 126.66, 126.74, 127.76, 127.83, 128.38, 133.19, 137.13, 143.07, 143.26, 156.43, 165.13

Example 5. Synthesis of Methyl 2-[4-({4-[(2-aminophenyl)carbamoyl]benzyl}carbamoyl)-1H-1,2,3-triazol-1-yl]acetate (6)

a) 4-[({[1-(2-methoxy-2-oxoethyl)-1H-1,2,3-triazol-4-yl]carbonyl}amino)methyl]benzoic acid

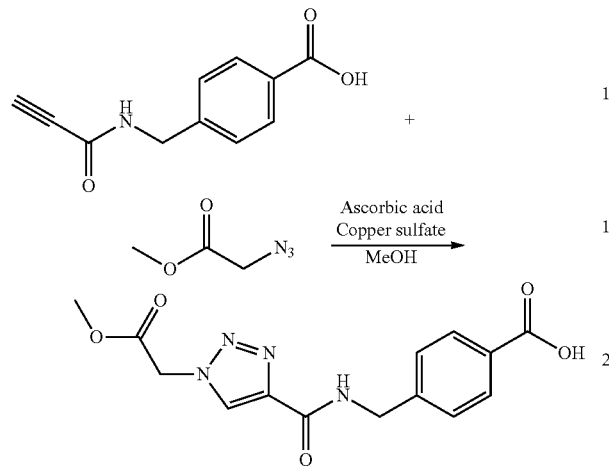

Methyl 2-azidoacetate (120 mg, 1.04 mmol) and 4-(propiolamidomethyl)benzoic acid (221 mg, 1.09 mmol) was dissolved in methanol (10 mL). CuSO$_4$*5H$_2$O (135 mg, 0.54 mmol) was added followed by ascorbic acid (289 mg, 1.64 mmol) added). A precipitate was formed. More water (5 ml) and more methanol (5 ml) was added. The reaction was stirred at room temperature overnight. EDTA-disodium salt (231 mg) was added to the reaction mixture and then it was diluted with dichloromethane and water. The layers were separated and the water layer was extracted first with dichloromethane and second with ethyl acetate. The combined ethyl acetate layers, containing almost pure product, was dried with sodium sulfate and evaporated (200 mg, 0.628 mmol, 58%). This was used without further purification in the synthesis of compound 6. $^1$H NMR (400 MHz, DMSO-d$_6$) δ ppm 3.73 (s, 3H) 4.52 (d, J=6.0 Hz, 2H) 5.49 (s, 2H) 7.42 (d, J=8.1 Hz, 2H) 7.90 (d, J=8.1 Hz, 2H) 8.58 (s, 1H) 9.24 (t, J=5.5 Hz, 1H) 12.86 (br. s., 1H). $^{13}$C NMR (101 MHz, DMSO-d$_6$) δ ppm 41.82, 50.56, 52.65, 127.24, 128.04, 129.39, 142.67, 144.69, 159.71, 167.19, 167.44. MS [M−H]$^−$: 317.3791 (calc 317.0891)

b) Methyl 2-[4-({4-[(2-aminophenyl)carbamoyl]benzyl}carbamoyl)-1H-1,2,3-triazol-1-yl]acetate (6)

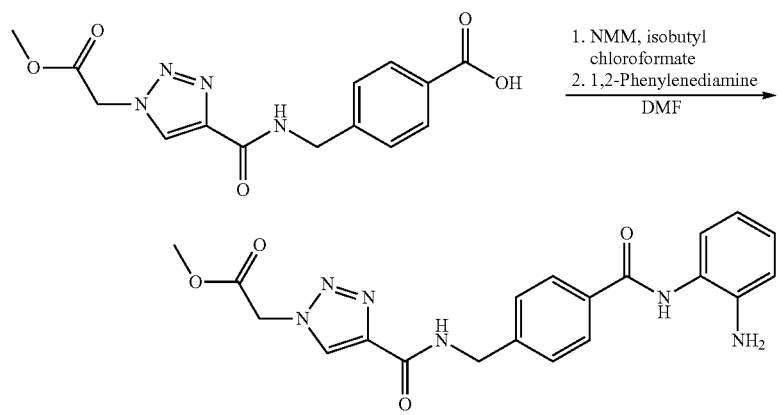

4-[({[1-(2-methoxy-2-oxoethyl)-1H-1,2,3-triazol-4-yl]carbonyl}amino)methyl]benzoic acid (113 mg, 0.356 mmol) and N-methylmorpholine (50 μl, 0.53 mmol) was dissolved in DMF (10 mL) and cooled to ca −10° C. in an ice/salt bath. Isobutyl chloroformate (ca 0.05 ml, 0.4 mmol) was added. After 15 min, 1,2-phenylenediamine (68 mg, 0.63 mmol) was added. After an additional 15 min, the cooling was removed and the mixture was left at room temperature overnight. The reaction mixture was diluted with dichloromethane, extracted with HCl (1 M). The water layer was basified with NaOH (5 M) and extracted with dichloromethane. The organic layer was dried with sodium sulfate and evaporated to dryness to yield the crude product. Recrystallization from methanol yielded pure product (7 mg, 0.017 mmol, 5%).

$^1$H NMR (400 MHz, DMSO-d$_6$) δ ppm 3.73 (s, 3H) 4.53 (d, J=6.0 Hz, 2H) 4.88 (br. s., 2H) 5.49 (s, 2H) 6.59 (t, J=7.6 Hz, 1H) 6.78 (d, J=8.0 Hz, 1H) 6.97 (t, J=7.6 Hz, 1H) 7.16 (d, J=7.6 Hz, 1H) 7.44 (d, J=8.0 Hz, 2H) 7.93 (d, J=8.0 Hz, 2H) 8.58 (s, 1H) 9.24 (t, J=6.5 Hz, 1H) 9.60 (s, 1H). $^{13}$C NMR (101 MHz, DMSO-d$_6$) δ ppm 41.79, 50.54, 52.64, 116.10, 116.23, 123.33, 126.42, 126.62, 127.03, 127.78, 127.99, 133.15, 142.71, 143.07, 159.65, 165.13, 167.44. MS [M+H]$^+$: 409.79 (calc 409.16)

Example 6. Synthesis of N'-(2-aminophenyl)-N$^4$-((4-(dimethylamino)phenyl)amino)-terephthalamide (7)

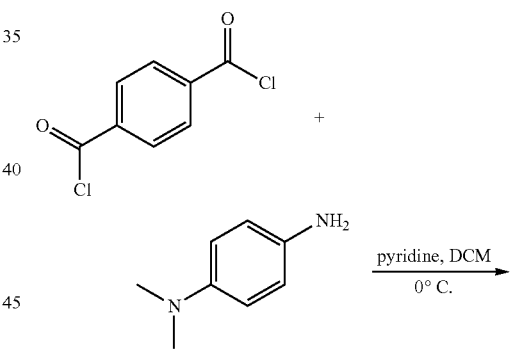

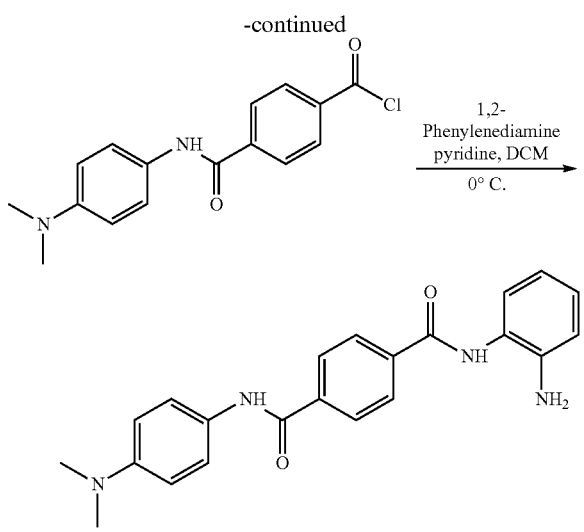

Terephthaloyl chloride (1.00 g, 4.91 mmol) was dissolved in dichloromethane (30 ml) at 0° C. N,N-dimethylbenzene-1,4-diamine (0.74 g, 5.41 mmol) and pyridine (0.40 ml, 4.95 mmol) in dichloromethane (20 ml) was added dropwise at 0° C., the cooling was removed and the reaction mixture was left at room temperature overnight. Half of this reaction mixture was added dropwise to a solution of 1,2-phenylenediamine (1.26 g, 11.7 mmol) and pyridine (0.50 mL, 6.2 mmol) in dichloromethane (20 ml) at 0° C. The cooling was removed and the reaction mixture was allowed to attain room temperature and was stirred for an additional 2 hrs and then diluted with dichloromethane. A precipitate that was formed in the reaction was filtered off, the filtrate was washed with water and extracted with HCl (1 M). The acidic water layer was basified with NaOH (5 M), extracted with dichloromethane. The organic layer was dried with sodium sulfate and evaporated to dryness. Recrystallization from methanol yielded pure product (245 mg, 0.654 mmol, 27%). $^1$H NMR (400 MHz, DMSO-$d_6$) δ ppm 2.88 (s, 6H) 4.98 (s, 2H) 6.60 (t, J=7.6 Hz, 1H) 6.73 (d, J=9.1 Hz, 2H) 6.80 (d, J=8.1 Hz, 1H) 6.97 (t, J=7.6 Hz, 1H) 7.20 (d, J=7.6 Hz, 1H) 7.63 (d, J=9.1 Hz, 2H) 8.06-8.17 (m, 4H) 9.93 (s, 1H) 10.22 (s, 1H)

Example 7. Synthesis of $N^1,N^4$-Bis(2-aminophenyl)terephthalamide (8)

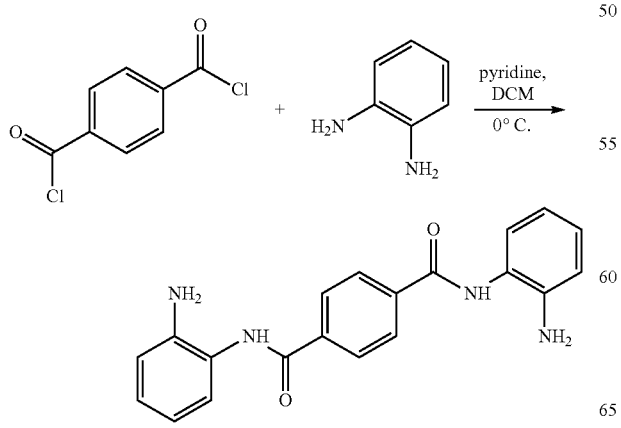

Terephthaloyl chloride in dichloromethane (30 ml) was added dropwise to a solution of 1,2-phenylenediamine (1.85 g, 17.11 mmol) and pyridine (1.5 mL) in dichloromethane (60 ml) at 0° C. The reaction mixture was allowed to attain room temperature and was stirred for an additional hour and then diluted with dichloromethane. A precipitate that was formed in the reaction was filtered off and the filtrate was washed with water, extracted with HCl (1 M). The water layer was basified with NaOH (5 M) and extracted with dichloromethane. The organic layer was dried with sodium sulfate and evaporated to dryness. Recrystallization from ethanol yielded a pure product (101 mg, 0.291 mmol, 7%). $^1$H NMR (400 MHz, DMSO-$d_6$) δ ppm 4.94 (br. s., 4H) 6.62 (t, J=7.3 Hz, 2H) 6.81 (d, J=8.0 Hz, 2H) 7.00 (dd, J=8.0, 7.2 Hz, 2H) 7.20 (d, J=7.5 Hz, 2H) 8.11 (s., 4H) 9.81 (s., 2H)
$^{13}$C NMR (101 MHz, DMSO-$d_6$) δ ppm 116.16, 116.28, 123.05, 126.72, 126.86, 127.74, 137.02, 143.28, 164.76

Example 8. Synthesis of $N^1$-(2-aminophenyl)-$N^5$-(4-(dimethylamino)phenyl)glutaramide (9)

a) 5-{[4-(dimethylamino)phenyl]amino}-5-oxopentanoic acid

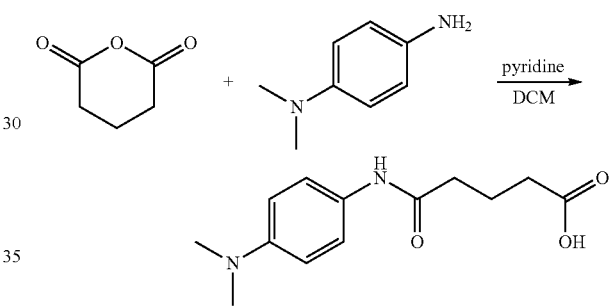

To a stirred solution of N,N-dimethylbenzene-1,4-diamine (1.67 g, 12.3 mmol) in dichloromethane (30 mL) was added pyridine (0.8 mL, 10.0 mmol) followed by glutaric anhydride (1.14 g, 10.0 mmol) in dichloromethane (10 mL). The reaction was stirred at room temperature overnight. The mixture was diluted with dichloromethane and extracted with sodium hydrogen carbonate (aq, sat). The water layer was adjusted to ca pH 5 with HCl and was extracted with dichloromethane and ethyl acetate. The combined organic layers was dried with sodium sulfate and evaporated. Recrystallization from methanol yielded pure product (454 mg, 1.81 mmol, 18%). $^1$H NMR (400 MHz, DMSO-$d_6$) δ ppm 1.79 (quin, J=7.3 Hz, 2H) 2.27 (m, 4H) 2.82 (s, 6H) 6.66 (d, J=9.1 Hz, 2H) 7.38 (d, J=9.1 Hz, 2H) 9.56 (s, 1H) 12.05 (br. s., 1H). $^{13}$C NMR (101 MHz, DMSO-$d_6$) δ ppm 20.63, 33.06, 35.24, 40.54, 112.68, 120.58, 129.22, 146.93, 169.84, 174.19 b) $N^1$-(2-aminophenyl)-$N^5$-(4-(dimethylamino)phenyl)glutaramide (9)

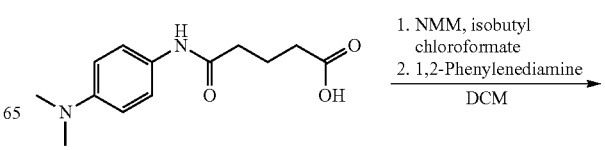

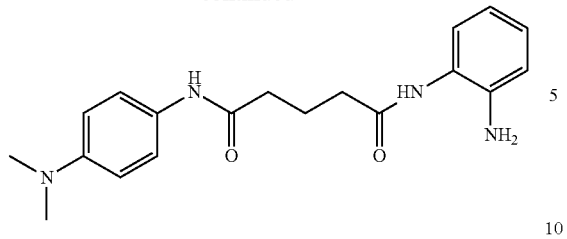

N-Methylmorpholine (138 μL, 1.25 mmol)) was added to a stirred solution of 5-{[4-(dimethylamino)phenyl]amino}-5-oxopentanoic acid (313 mg, 1.25 mmol) in dichloromethane (20 mL) at room temperature. After 30 min, isobutyl chloroformate (0.2 mL, 1.5 mmol) was added and after 10 min followed by 1,2-phenylenediamine (143 mg, 1.32 mmol) in dichloromethane (5 ml). The reaction was left at room temperature overnight, diluted with dichloromethane and water. The mixture was extracted with HCl (1 M). The water layer was basified with NaOH (5 M) and extracted with dichloromethane. The organic layer was evaporated to give the crude product. Recrystallization from ethanol yielded pure product (55.1 mg, 0.162 mmol, 13%). $^1$H NMR (400 MHz, DMSO-$d_6$) δ 1.89 (t, J=7.3 Hz, 2H) 2.32 (t, J=7.6 Hz, 2H) 2.37 (t, J=7.3 Hz, 2H) 2.83 (s, 6H) 4.88 (br. s, 2H) 6.53 (t, J=7.3 Hz, 1H) 6.67 (d, J=9.1 Hz, 2H) 6.71 (d, J=8.1 Hz, 1H) 6.89 (t, J=7.6 Hz, 1H) 7.18 (d, J=7.6 Hz, 1H) 7.41 (d, J=9.1 Hz, 2H) 9.10 (s, 1H) 9.60 (s, 1H). $^{13}$C NMR (101 MHz, DMSO-$d_6$) δ ppm 21.35, 35.05, 35.50, 40.53, 112.65, 115.80, 116.09, 120.53, 123.49, 125.33, 125.66, 129.29, 141.85, 146.86, 169.96, 170.75

Example 9. Synthesis of (9H-fluoren-9-yl)methyl (4-((2-aminophenyl)carbamoyl)-benzyl)carbamate (10)

a) 4-({[(9H-fluoren-9-ylmethoxy)carbonyl]amino}methyl)benzoic acid

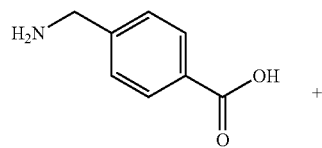 +

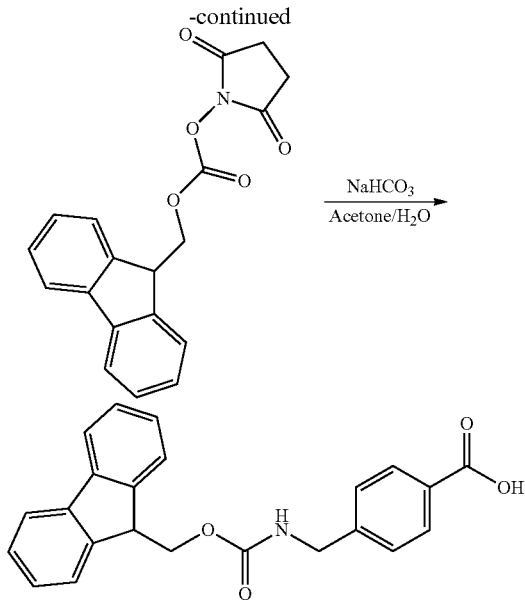

4-(Aminomethyl)benzoic acid (304 mg, 2.0 mmol) was stirred in 10% Sodium hydrogencarbonate (sat aq, 10 ml). N-(9-Fluorenylmethoxycarbonyloxy)succinimide (680 mg, 2.0 mmol) and acetone (10 ml) was added and thick suspension was formed. Water (10 ml) was added to give an almost clear mixture that was stirred at room temperature over week-end. The mixture was washed with dichloromethane (a thick precipitate was formed in the water layer). The water layer was acidified with HCl (1 M) and extracted with dichloromethane (the precipitate moved into the dichloromethane layer). The precipitate was filtered off, dissolved in acetone and the insoluble material was filtered off. This latter filtrate was evaporated and dried on pump to yield a pure product (174 mg, 0.466 mmol, 23%). $^1$H NMR (400 MHz, DMSO-$d_6$) δ ppm 4.25 (m, 3H) 4.38 (d, J=6.6 Hz, 2H) 7.26-7.46 (m, 6H) 7.70 (d, J=7.6 Hz, 2H) 7.81-7.99 (m, 5H) 12.85 (br. s., 1H). $^{13}$C NMR (101 MHz, DMSO-$d_6$) δ ppm 43.55, 46.82, 65.33, 120.11, 125.14, 126.96, 127.03, 127.59, 129.37, 140.78, 143.86, 144.90, 156.41, 167.19.

b) (9H-fluoren-9-yl)methyl (4-((2-aminophenyl)carbamoyl)benzyl)carbamate (10)

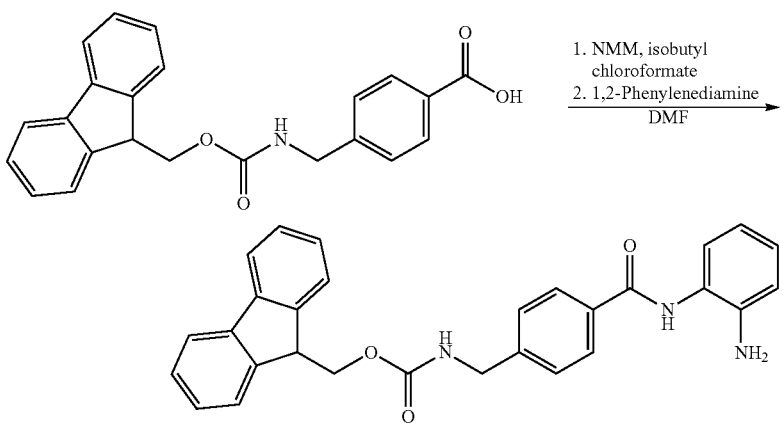

4-({[(9H-fluoren-9-ylmethoxy)carbonyl]amino}methyl) benzoic acid (397.3 mg, 1.06 mmol) was evaporated with toluene and then dissolved in DMF (10 ml). N-Methylmorpholine (140, 1.27 mmol) was added, followed by isobutyl chloroformate (0.18 ml, 1.4 mmol). After 15 min, 1,2-Phenylendiamine (170 mg, 1.57 mmol) was added. The mixture was stirred at room temperature overnight and then evaporated to give the crude product as oil. This oil was dissolved in dichloromethane and crystals was formed. Recrystallization from methanol yielded pure product (254 mg, 0.548 mmol, 51%)

$^1$H NMR (400 MHz, DMSO-$d_6$) δ ppm 4.26 (m, 3H) 4.39 (d, J=6.6 Hz, 2H) 4.90 (br. s., 2H) 6.61 (t, J=7.3 Hz, 1H) 6.80 (d, J=7.6 Hz, 1H) 6.98 (t, J=7.6 Hz, 1H) 7.19 (d, J=8.1 Hz, 1H) 7.35 (d, J=5.5 Hz, 4H) 7.43 (t, J=7.0 Hz, 2H) 7.72 (d, J=7.6 Hz, 2H) 7.92 (m, 5H) 9.63 (s, 1H)

$^{13}$C NMR (101 MHz, DMSO-$d_6$) δ ppm 43.51, 46.80, 65.33, 116.12, 116.25, 120.12, 123.34, 125.12, 126.44, 126.65, 126.69, 127.04, 127.60, 127.79, 133.15, 140.76, 143.10, 143.27, 143.86, 156.38, 165.10

Example 10. Synthesis of 4-(((((pyridin-3-yl-methoxy)carbonyl)amino)methyl)benzoic acid (11)

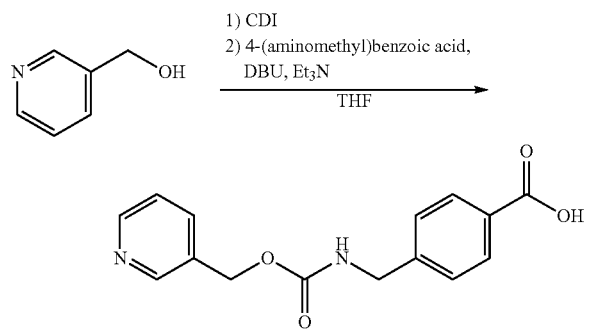

Prepared according the procedure described by Lalji Gediya et al:

$^1$H NMR (400 MHz, DMSO-$d_6$) δ ppm 4.28 (d, J=6.0 Hz, 2H) 5.10 (s, 2H) 7.36 (d, J=8.0 Hz, 2H) 7.41 (dd, J=7.5, 5.0 Hz, 1H) 7.78 (d, J=7.8 Hz, 1H) 7.90 (d, J=8.0 Hz, 2H) 7.95 (t, J=5.9 Hz, 1H) 8.53 (d, J=3.8 Hz, 1H) 8.59 (s, 1H) 12.89 (br. s., 1H). $^{13}$C NMR (101 MHz, DMSO-$d_6$) δ ppm 43.63, 63.27, 123.52, 126.99, 129.36, 129.39, 132.65, 135.76, 144.76, 149.10, 149.13, 156.25, 167.15. MS [M–H]$^-$: 285.25 (calc 285.09).

Example 11. Synthesis of N-(2-Hydroxyphenyl) benzamide (14)

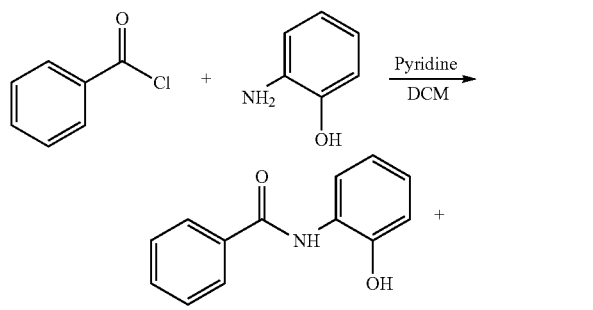

To a solution of 2-aminophenol (0.59 g, 5.4 mmol) in dichloromethane (10 mL) and pyridine (0.50 mL, 0.62 mmol), at 0° C. was added benzoyl chloride (0.65 mL, 5.6 mmol) in dichloromethane (10 mL), and the mixture was stirred for 3 hrs. The reaction mixture was diluted with dichloromethane and washed with sodium hydrogen carbonate (aq, sat), dried with sodium sulfate and evaporated to dryness to give a crude mixture of N-(2-hydroxyphenyl) benzamide and 2-(benzoylamino)phenyl benzoate. Recrystallized from methanol also gave a mixture of these two compounds.

A mixture of combined mono- and di-benzoyl derivatives (400 mg) was dissolved in methanol (10 mL) and about 1 ml 30% sodium methoxide in methanol was added. When no more 2-(benzoylamino)phenyl benzoate could be detected by TLC, the reaction was neutralized with acetic acid and evaporated to dryness. The crude product was dissolved in dichloromethane and washed with sodium hydrogen carbonate (aq, sat) dried with sodium sulfate and evaporated to dryness to give a crude mixture of N-(2-hydroxyphenyl) benzamide. Several recrystallizations from methanol gave a pure product (69 mg). $^1$H NMR (400 MHz, DMSO-$d_6$) δ ppm 6.84 (t, J=7.6 Hz, 1H) 6.93 (d, J=8.1 Hz, 1H) 7.04 (td, J=7.7, 1.4 Hz, 1H) 7.53 (t, J=7.6 Hz, 2H) 7.60 (t, J=7.3 Hz, 1H) 7.70 (dd, J=8.00, 1.4 Hz, 1H) 7.98 (d, J=7.6 Hz, 2H) 9.52 (s, 1H) 9.74 (s, 1H). $^{13}$C NMR (101 MHz, DMSO-$d_6$) δ ppm 115.99, 119.03, 124.09, 125.68, 125.87, 127.48, 128.50, 131.65, 134.38, 149.32, 165.25.

Example 12. Synthesis of N-(2-methoxyphenyl)benzamide (15)

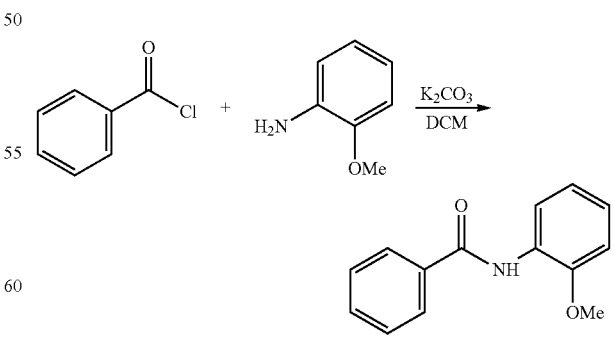

To a stirred mixture of anisidine (1.128 mL, 10.0 mmol) and potassium carbonate (1.45 g, 10.5 mmol) in dichloromethane (40 mL), benzoylchloride (1.16 mL, 10.0 mmol) added. After ca 30 s a precipitate was formed. The mixture was left at room temperature overnight and the diluted with dichloromethane, washed with water, HCl (1 M) and sodium hydrogen carbonate (aq, sat). The organic layer was dried with sodium sulfate and evaporated. Silica gel chromatography (hexane:ethyl acetate:dichlormetane gradient) yielded pure N-(2-methoxyphenyl)benzamide (2.2 g, 9.7 mmol, 97%) as an oil. $^1$H NMR (400 MHz, chloroform-d) δ ppm 3.94 (s, 3H) 6.94 (d, J=7.6 Hz, 1H) 7.04 (td, J=7.7, 1.4 Hz, 1H) 7.10 (td, J=7.6, 1.5 Hz, 1H) 7.47-7.60 (m, 3H) 7.89-7.94 (m, 2H) 8.53-8.57 (m, 1H) 8.57 (br. s, 1H). $^{13}$C NMR (101 MHz, chloroform-d) δ ppm 56.06, 110.18, 120.09, 121.46, 124.11, 127.29, 128.05, 128.99, 131.92, 135.59, 148.39, 165.49.

Example 13. Synthesis of N-(2-aminoethyl)-benzamide (17)

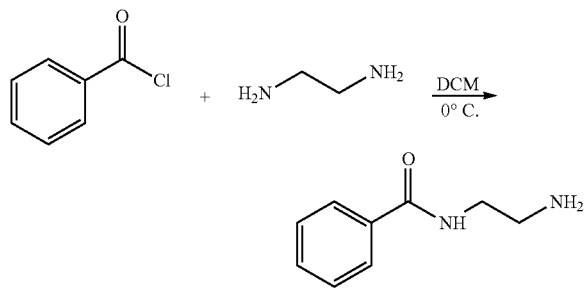

Ethylenediamine (2.00 mL, 30.0 mmol) was dissolved in dichloromethane (100 mL) benzoyl chloride (1.16 mL, 10 mmol) in dichloromethane (20 mL) added dropwise at 0° C. A white precipitate was formed and the reaction mixture was left at rt overnight. The precipitate was filtered off and washed with dichloromethane. The filtrate was evaporated to give a mixture of N-(2-aminoethyl)-benzamide and N,N'-ethane-1,2-diyldibenzamide as an oil. The oil was triturated with ethyl acetate, a precipitate was formed which was filtered off. The filtrate was concentrated and subsequently purified on silica gel chromatography (hexane:dichlorometane:methanol gradient). Further purification with repeated triturations/crystallizations from dichloromethane and methanol gave a pure sample of N-(2-aminoethyl)-benzamide. $^1$H NMR (400 MHz, DMSO-d$_6$) δ ppm 1.56-2.26 (m, 2H) 2.69 (t, J=6.50 Hz, 2H) 3.27 (td, J=6.60, 6.00 Hz, 2H) 7.41-7.54 (m, 3H) 7.83-7.87 (m, 2H) 8.41 (t, J=6.00 Hz, 1H); $^{13}$C NMR (101 MHz, DMSO-d$_6$) δ ppm 41, 30, 43.02, 127.15, 128.17, 130.96, 134.69, 166.34

Example 14. Synthesis of N-(2-aminoethyl)-4-methoxybenzamide (18)

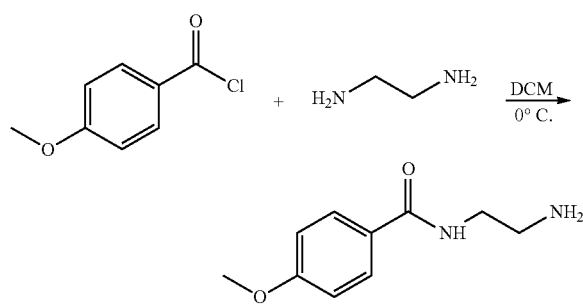

Ethylenediamine (0.20 mL, 3.0 mmol) was dissolved in dichloromethane (20 mL) 4-methoxybenzoyl chloride (251 mg, 1.47 mmol) in dichloromethane (5 mL) was added dropwise at 0° C. The reaction mixture was left at rt a few days. The reaction mixture was diluted with dichloromethane and extracted with hydrochloric acid (1 M). The water layer basified with sodium hydroxide (aq) and extracted with dichloromethane to yield a crude mixture of N-(2-aminoethyl)-4-methoxybenzamide and N,N'-ethane-1,2-diylbis(4-methoxybenzamide). A pure sample of N-(2-aminoethyl)-4-methoxybenzamide was obtained by repeated triturations/crystallizations from dichloromethane and methanol. $^1$H NMR (400 MHz, DMSO-d$_6$) δ ppm 2.99 (t, J=6.29 Hz, 2H) 3.49 (td, J=6.30, 5.50 Hz, 2H) 3.81 (s, 3H) 7.00 (d, J=9.06 Hz, 2H) 7.94 (br. s., 3H) 7.85 (d, J=9.06 Hz, 2H) 8.53 (t, J=5.54 Hz, 1H); $^{13}$C NMR (101 MHz, DMSO-d$_6$) δ ppm 37.17, 38.73, 55.35, 113.45, 126.28, 129.17, 161.70, 166.41

Example 15

Fold induction assays in the MN8CampLuc reporter cell line with compounds 1-11 and 13-15 showing high induction of the CAMP gene with most of compounds 1-10 while 13 gave considerably lower induction and the 11 and 14-15 give virtually no induction (FIG. 2.).

Example 16

Comparative fold induction assays in the MN8CampLuc reporter cell line with and without pre-differentiation of cells by treatment with galactose showing that substantial induction of the CAMP gene irrespective of if cells are pre-differentiated or not (FIG. 3). Also shown is that the known HDAC inhibitor Vorinostat (12) gives little induction which on not pre-differentiated may be mainly due to affecting the differentiation.

Example 17

Fold induction assays in the MN8CampLuc reporter cell line with compound 5 compared to compounds 12 and 19 showing lack of correlation between HDAC inhibitory ability and induction of LL-37 (FIG. 4).

Example 18

Fold induction assays in the MN8CampLuc reporter cell line with compound 1 and 2 compared to compounds 17 and 18 showing abolition of induction when the aromatic diamine is replaced with an aliphatic one (FIG. 5) and an additional example (16) showing that the linker to the diamine can be variable (also seen in FIG. 2 for compound 9) albeit at a cost of inducing ability.

Example 19

Further testing of pyridin-3-ylmethyl (4-((2-aminophenyl)carbamoyl)benzyl)carbamate (5, entinostat) in the reporter cell line. FIG. 6 shows the synergistic effect of 5 in combination with VitD. Interestingly, co-incubation with PBA (13) reduces entinostat-elicited induction: this suggests some commonality in the mechanism for PBA and 5, although the latter is likely to work also via additional mechanism(s).

Example 20

Pyridin-3-ylmethyl (4-((2-aminophenyl)carbamoyl)benzyl)carbamate (5) induces the CAMP gene in HT29 parental cells. RT-PCR shows induction of the CAMP gene at mRNA level by 5 (FIG. 7). The results confirm synergy with Vitamin D.

Example 21

PBA and pyridin-3-ylmethyl (4-((2-aminophenyl)carbamoyl)benzyl)carbamate (5) increase the CAMP gene expression with different time course as monitored via mRNA in HT-29 cells (FIG. 8). RT-PCR on the parental HT-29 cell line shows a different time course for the induction elicited by PBA (13) and 5. PBA induced a gradual increase of the CAMP gene expression. Pyridin-3-ylmethyl (4-((2-aminophenyl)carbamoyl)benzyl)carbamate (5) did not induce at 4 and 8 h, but induction was prominent at 24 and 48 h.

Example 22

Experiments showing that compound 5 also can induce autophagy in HEK-293 cells. Treatment with 10 µM Entinostat can upregulate the expression of autophagy related gene Beclin-1 and Atg5 (FIG. 9, upper panel) together with LC3 expression in its membrane form (LC3-II, FIG. 9, lower panel). Rapamycin was used as a positive control.

Results

We used MN8CampLuc cells to screen a panel of different compounds. All the compounds were tested at different concentrations. All the compounds of the general structure (I) as exemplified by structures 1-10 and 16 (FIG. 1) tested were able to induce LL-37-luciferase (a construct producing the pro-form i.e. hCAP18, fused to luciferase) to the same level or more than the positive control PBA (FIG. 2) and typically at a lower concentration of the inducer.

The induction with pyridin-3-ylmethyl (4-((2-aminophenyl)carbamoyl)benzyl)carbamate (5) required the lowest concentration and was effective already at µM concentrations followed by compounds 1, 2, 4 and 6 that required a slightly higher concentration to reach similar increases in fold induction (FIG. 2). The compound pyridin-3-ylmethyl (4-((2-aminophenyl)carbamoyl)benzyl)carbamate (5, Entinostat) gave an induction at 0.625-5 µM, that was considerably higher than that found with PBA (13) at 2-4 mM concentration (FIG. 2) i.e. at about 3 orders of magnitude lower concentration than PBA.

The known CAMP inducers PBA and BA are inhibitors of class I HDAC and hence they promote histone acetylation (9, 11). Histone acetylation is known to play a critical role in gene transcriptional regulation by causing chromatin relaxation and allowing the binding of transcription factors to DNA regulatory elements (25). However the molecular mechanism for BA- and PBA-elicited induction of the CAMP gene is not clear, since it has been shown to be secondary and to depend on the de novo synthesis of unknown specific factor(s) (11) as opposed to simply facilitating binding of pre-existing factors. It is also clear that PBA and BA are much more powerful inducers than the corresponding hydroxamic acids (32) although these are considerably more powerful HDAC inhibitors (33), suggesting that the main mechanism for the induction with PBA and BA is not via HDAC inhibition.

Several of the newly provided inducers are also known to be HDAC inhibitors. However, compounds such as the known non-selective HDAC inhibitor Vorinostat (12) was a poor inducer although it is a more potent HDAC inhibitor (26) (27) and did not elicit the same effect on LL-37 expression compared to compounds of the new class that are less active HDAC inhibitors but much more active as inducers (FIG. 3). This suggests that the main mechanism for induction is not gene activation through HDAC inhibition. Additional support for this is that the potent HDAC inhibitors Vorinostat (12) and Trichostatin A (19) give much less fold induction than compound 5 (Entinostat, pyridin-3-ylmethyl (4-((2-aminophenyl)carbamoyl)benzyl)carbamate (FIG. 4, left panel) although all known $IC_{50}$ values for HDAC inhibition shows that 12 and 19 are considerably more powerful HDAC inhibitors (FIG. 4, right panel). Although HDAC inhibitors can give some limited induction of antimicrobial peptides, it seems clear that the main inducing ability of the new class of inducers represented by compounds 1-10 and 16 is not via a mechanism involving HDAC inhibition.

Comparative studies with similar compounds reveal that the phenylenediamine moiety is essential and that one nitrogen cannot be replaced by an oxygen without complete or significant loss of the induction ability (FIG. 2, compounds 14 and 15) nor can the aromatic diamino-moiety be replaced by a simple aliphatic diamine (FIG. 5, compounds 17 and 18). In addition, truncating the molecule by simply leaving out the diamine moiety (compound 11) results in complete inactivity (FIG. 2).

Synergism with Vitamin D, as is known for PBA (13), was also found with pyridin-3-ylmethyl (4-((2-aminophenyl)carbamoyl)benzyl)carbamate (5, Entinostat) in the reporter cell line (FIG. 6). The induction by pyridin-3-ylmethyl (4-((2-aminophenyl)carbamoyl)-benzyl)carbamate (5, Entinostat) as well as the synergism with Vitamin D is also evident in the parental cell line (HT-29) giving enhanced transcription of the CAMP gene (FIGS. 7 and 8).

As seen from fold induction of marker genes and emergence of LC-3 (FIG. 9), pyridin-3-ylmethyl (4-((2-aminophenyl)carbamoyl)benzyl)carbamate (5, Entinostat) also stimulates autophagy, via induction of LL-37 or via another pathway, thereby additionally contributing to the removal of microbial infection.

REFERENCES

1. Cederlund A, Gudmundsson G H, Agerberth B. 2011. Antimicrobial peptides important in innate immunity. The FEBS journal 278:3942-3951.
2. Zasloff M. 2002. Antimicrobial peptides of multicellular organisms. Nature 415:389-395.
3. Zaiou M, Gallo R L. 2002. Cathelicidins, essential gene-encoded mammalian antibiotics. J Mol Med (Berl) 80:549-561.
4. Ganz T. 2003. Defensins: antimicrobial peptides of innate immunity. Nat Rev Immunol 3:710-720.
5. Brogden K A. 2005. Antimicrobial peptides: pore formers or metabolic inhibitors in bacteria? Nat Rev Microbiol 3:238-250.
6. Hancock R E, Sahl H G. 2006. Antimicrobial and host-defense peptides as new anti-infective therapeutic strategies. Nat Biotechnol 24:1551-1557.
7. Agerberth B, Charo J, Werr J, Olsson B, Ida F, Lindbom L, Kiessling R, Jornvall H, Wigzell H, Gudmundsson G H. 2000. The human antimicrobial and chemotactic peptides LL-37 and alpha-defensins are expressed by specific lymphocyte and monocyte populations. Blood 96:3086-3093.

8. Yang D, Chertov O, Oppenheim J J. 2001. The role of mammalian antimicrobial peptides and proteins in awakening of innate host defenses and adaptive immunity. Cell Mol Life Sci 58:978-989.
9. Schauber J, Svanholm C, Termen S, Iffland K, Menzel T, Scheppach W, Melcher R, Agerberth B, Luhrs H, Gudmundsson G H. 2003. Expression of the cathelicidin LL-37 is modulated by short chain fatty acids in colonocytes: relevance of signalling pathways. Gut 52:735-741.
10. Raqib R, Sarker P, Bergman P, Ara G, Lindh M, Sack D A, Nasirul Islam K M, Gudmundsson G H, Andersson J, Agerberth B. 2006. Improved outcome in shigellosis associated with butyrate induction of an endogenous peptide antibiotic. Proceedings of the National Academy of Sciences of the United States of America 103:9178-9183.
11. Steinmann J, Halldorsson S, Agerberth B, Gudmundsson G H. 2009. Phenylbutyrate induces antimicrobial peptide expression. Antimicrobial agents and chemotherapy 53:5127-5133.
12. Wang T T, Nestel F P, Bourdeau V, Nagai Y, Wang Q, Liao J, Tavera-Mendoza L, Lin R, Hanrahan J W, Mader S, White J H. 2004. Cutting edge: 1,25-dihydroxyvitamin D3 is a direct inducer of antimicrobial peptide gene expression. J Immunol 173:2909-2912.
13. Gombart A F, Borregaard N, Koeffler H P. 2005. Human cathelicidin antimicrobial peptide (CAMP) gene is a direct target of the vitamin D receptor and is strongly up-regulated in myeloid cells by 1,25-dihydroxyvitamin D3. FASEB J 19:1067-1077.
14. Weber G, Heilborn J D, Chamorro Jimenez C I, Hammarsjo A, Torma H, Stahle M. 2005. Vitamin D induces the antimicrobial protein hCAP18 in human skin. The Journal of investigative dermatology 124:1080-1082.
15. Boucher H W, Talbot G H, Bradley J S, Edwards J E, Gilbert D, Rice L B, Scheld M, Spellberg B, Bartlett J. 2009. Bad bugs, no drugs: no ESKAPE! An update from the Infectious Diseases Society of America. Clin Infect Dis 48:1-12.
16. Spellberg B, Guidos R, Gilbert D, Bradley J, Boucher H W, Scheld W M, Bartlett J G, Edwards J, Jr. 2008. The epidemic of antibiotic-resistant infections: a call to action for the medical community from the Infectious Diseases Society of America. Clin Infect Dis 46:155-164.
17. Marr A K, Gooderham W J, Hancock R E. 2006. Antibacterial peptides for therapeutic use: obstacles and realistic outlook. Current opinion in pharmacology 6:468-472.
18. Fehlbaum P, Rao M, Zasloff M, Anderson G M. 2000. An essential amino acid induces epithelial beta-defensin expression. Proceedings of the National Academy of Sciences of the United States of America 97:12723-12728.
19. Gudmundsson G H, Agerberth B, Odeberg J, Bergman T, Olsson B, Salcedo R. 1996. The human gene FALL39 and processing of the cathelin precursor to the antibacterial peptide LL-37 in granulocytes. Eur J Biochem 238:325-332.
20. Cederlund A, Agerberth B, Bergman P. 2010. Specificity in killing pathogens is mediated by distinct repertoires of human neutrophil peptides. Journal of innate immunity 2:508-521.
21. Yoshio H, Tollin M, Gudmundsson G H, Lagercrantz H, Jornvall H, Marchini G, Agerberth B. 2003. Antimicrobial polypeptides of human vernix caseosa and amniotic fluid: implications for newborn innate defense. Pediatric research 53:211-216.
22. Zhang J H, Chung T D, Oldenburg K R. 1999. A Simple Statistical Parameter for Use in Evaluation and Validation of High Throughput Screening Assays. J Biomol Screen 4:67-73.
23. Szilagyi A, Blasko B, Szilassy D, Fust G, Sasvari-Szekely M, Ronai Z. 2006. Real-time PCR quantification of human complement C4A and C4B genes. BMC genetics 7:1.
24. Park K, Elias P M, Oda Y, Mackenzie D, Mauro T, Holleran W M, Uchida Y. 2011. Regulation of cathelicidin antimicrobial peptide expression by an endoplasmic reticulum (ER) stress signaling, vitamin D receptor-independent pathway. J Biol Chem 286:34121-34130.
25. Licciardi P V, Kwa F A, Ververis K, Di Costanzo N, Balcerczyk A, Tang M L, El-Osta A, Karagiannis T C. 2012. Influence of natural and synthetic histone deacetylase inhibitors on chromatin. Antioxidants & redox signaling 17:340-354.
26. Hu E, Dul E, Sung C M, Chen Z, Kirkpatrick R, Zhang G F, Johanson K, Liu R, Lago A, Hofmann G, Macarron R, de los Frailes M, Perez P, Krawiec J, Winkler J, Jaye M. 2003. Identification of novel isoform-selective inhibitors within class I histone deacetylases. J Pharmacol Exp Ther 307:720-728.
27. Richon V M, Emiliani S, Verdin E, Webb Y, Breslow R, Rif kind R A, Marks P A. 1998. A class of hybrid polar inducers of transformed cell differentiation inhibits histone deacetylases. Proceedings of the National Academy of Sciences of the United States of America 95:3003-3007.
28. NIH US 2012, posting date. clinicaltrials.gov. [Online.]
29. Prince H M, Bishton M J, Harrison S J. 2009. Clinical studies of histone deacetylase inhibitors. Clin Cancer Res 15:3958-3969.
30. Liu P T, Stenger S, Tang D H, Modlin R L. 2007. Cutting edge: vitamin D-mediated human antimicrobial activity against *Mycobacterium tuberculosis* is dependent on the induction of cathelicidin. J Immunol 179:2060-2063.
31. Sarker P, Ahmed S, Tiash S, Rekha R S, Stromberg R, Andersson J, Bergman P, Gudmundsson G H, Agerberth B, Raqib R. 2011. Phenylbutyrate counteracts *Shigella* mediated downregulation of cathelicidin in rabbit lung and intestinal epithelia: a potential therapeutic strategy. PLoS One 6:e20637.
32. Nylén F, Miraglia E, Cederlund A, Ottosson H, Stromberg R, Gudmundsson G H, Agerberth B. 2014. Boosting innate immunity: Development and validation of a cell-based screening assay to identify LL-37 inducers. *Innate Immunity* 20, 364-376.
33. Fass D M, Shah R, Ghosh B, Hennig K, Norton S, Zhao W-N, Reis S A, Klein P S, Mazitschek R, Maglathlin R L, Lewis T A, Haggarty S J. 2010. Short-Chain HDAC Inhibitors Differentially Affect Vertebrate Development and Neuronal Chromatin. *ACS Med. Chem. Lett.* 2, 39-42.

The invention claimed is:
1. A method of treatment of a microbial infection in an animal, which method comprises administering to the animal a compound of formula (I):

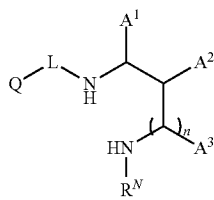

(I)

wherein:
Q is selected from Q1, Q2, Q3, Q4, Q5 and Q6:

Q1
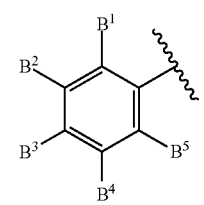

Q2
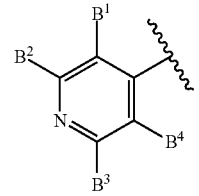

Q3
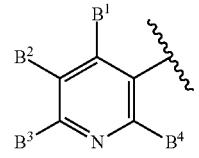

Q4
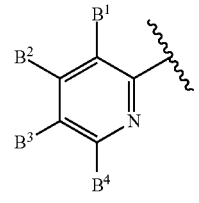

Q5
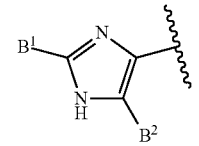

Q6
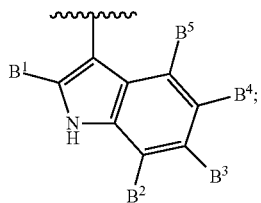

n is 0 or 1;
L is selected from —(CH$_2$)$_m$—, —C(=O)—, —(CH$_2$)$_m$—C(=O)—, —O—(CH$_2$)$_m$—C(=O)—, —O—C(=O)—(CH$_2$)$_m$—(C=O)—, —NH—C(=O)—, —NR—C(=O)—, —NH—(CH$_2$)$_m$—C(=O)—, —NR—(CH$_2$)$_m$—C(=O)—, —NH—C(=O)—(CH$_2$)$_m$—C(=O)—, —NR—C(=O)—(CH$_2$)$_m$—C(=O)—, —C(=O)—NH—(CH$_2$)$_m$—C(=O)—, and —(CH$_2$)$_m$—(CHR$^L$)—C(=O)—, where m is an integer from 1 to 4;

A and A$^2$, together with the atoms to which they are bound, form an optionally substituted phenyl, naphthalene or heteroaryl group;

A$^3$, if present, is selected from H and optionally substituted C$_{1-4}$alkyl;

R$^N$ is selected from H and optionally substituted$^3$ C$_{1-4}$alkyl;

one of B$^1$, B$^2$, B$^3$, B$^4$, and B$^5$ is a group of formula —X—R$^X$ and the others are independently selected from H and R$^B$;

wherein each —R$^B$ is independently selected from halogen, —CF$_3$, —R, —OH, —OR, —OCF$_3$, —C(=O)OH, —C(=O)OR, —C(=O)R, —OC(=O)R, —NH$_2$, —NHR, —NR$_2$, —NO$_2$, —C(=O)NH$_2$, —C(=O)NHR, C(=O)NR$_2$, —S(=O)R, —S(=O)$_2$R, —S(=O)$_2$NR$_2$, or —CN;

X is selected from a covalent bond or C$_{1-3}$alkylene;

R$^X$ is selected from —H, R$^{XX}$ or R$^{XY}$;

wherein:
R$^{XX}$ is halogen, —CF$_3$, —OH, —OR, —OCF$_3$, —C(=O)OH, —NO$_2$, —NH$_2$, —NHR, —NR$_2$, —C(=O)NH$_2$, —C(=O)NR$_2$, —S(=O)R, —S(=O)$_2$R, —S(=O)$_2$NR$_2$, or —CN; and R$^{XY}$ is a group of formula -L$^X$-R$^{YY}$;

wherein L$^x$ is selected from:
—NH—C(=O)—O—, —NH—C(=O)—NH—, —NH—C(=O)—
—O—C(=O)—NH—, —O—C(=O)—O—, —O—(C=O)—
—C(=O)—NH—, —C(=O)—O—, —C(=O)—;

and R$^{YY}$ is selected from C$_{1-4}$alkyl, C$_{3-6}$cycloalkyl, —C$_{6-14}$aryl, -L$^Y$-C$_{6-14}$aryl, -L$^Y$-O—C$_{6-14}$aryl-C$_{5-6}$heteroaryl, -L$^Y$-C$_{5-6}$heteroaryl, and -L$^Y$-O—C$_{5-6}$heteroaryl, wherein —L$^Y$— is C$_{1-3}$alkylene and wherein each of said groups is optionally substituted;

R$^L$ is selected from halogen, —R$^{LL}$, —CF$_3$, —OH, —OR$^{LL}$, —NO$_2$, —NH$_2$, —NHR$^{LL}$, —NR$_2$, —NH—C(=O)—R$^{LL}$, —NH—C(=O)—O—R$^{LL}$ wherein R$^{LL}$ is selected from —C$_{1-4}$alkyl, —C$_{3-6}$cycloalkyl, -Ph, —L$^L$-Ph, —C$_{5-6}$heteroaryl, -L$^L$-C$_{5-6}$heteroaryl wherein -L$^L$- is C$_{1-3}$alkylene;

and wherein each R is independently C$_{1-4}$alkyl.

2. A method according to claim 1, wherein R$^N$ is H.
3. A method according to claim 1, wherein n is 0.
4. A method according to claim 1, wherein Q is Q1.
5. A method according to claim 4, wherein B$^3$ is —X—R$^X$.
6. A method according to claim 4, wherein B$^1$, B$^2$, B$^4$ and B$^5$ are all H.
7. A method according to claim 1, wherein L is selected from —(CH$_2$)$_m$—, —C(=O)—, —NH—C(=O)—, —NR—C(=O)— and —NH—C(=O)—(CH$_2$)$_m$—C(=O)—.
8. A method according to claim 1, wherein X is independently: —CH$_2$—, —CH$_2$CH$_2$—, —CH$_2$CH$_2$CH$_2$—, —CH(CH$_3$)—, —CH(CH$_3$)CH$_2$—, —CH$_2$CH(CH$_3$)—, or —CH(CH$_2$CH$_3$)—.
9. A method according to claim 1, wherein R$^X$ is —R$^{XX}$, wherein R$^{XX}$ is independently: halogen (F, Cl, Br, I), —CF$_3$, —OH, —OR, —NO$_2$, or —OCF$_3$.

10. A method according to claim 1, wherein $R^X$ is —$R^{XY}$.

11. A method according to claim 10, wherein $L^X$ is independently: —NH—C(=O)—O—, —NH—C(=O)—NH—, —NH—C(=O)—, —O—C(=O)—NH—, or —C(=O)—NH—.

12. A method according to claim 1, wherein $R^{YY}$ is independently: -Ph, -$L^Y$-Ph, $C_{5-6}$heteroaryl, or -$L^Y$-$C_{5-6}$heteroaryl.

13. A method according to claim 1, wherein —$L^Y$— is independently: —$CH_2$—, —$CH_2CH_2$—, —$CH_2CH_2CH_2$—, —$CH(CH_3)$—, —$CH(CH_3)CH_2$—, —$CH_2CH(CH_3)$—, or —$CH(CH_2CH_3)$—.

14. A method according to claim 1, wherein $R^{YY}$ is independently: —$CH_2$-Ph, triazolyl, or —$CH_2$-pyridyl.

15. A method according to claim 14, wherein $R^{YY}$ is independently —$CH_2$-Ph, —$CH_2$-(3-pyridyl) or 1,2,3-triazol-1-yl.

16. A method according to claim 1, wherein $R^{YY}$ is substituted with one or more substituents selected from: —F, —Cl, —Br, —I, —R, —$CF_3$, —OH, —OR, —$OCF_3$, —$NO_2$, -$L^{YY}$-OH, -$L^{YY}$-OR, —$NH_2$, —NHR, —$NR_2$, -$L^{YY}$-$NH_2$, -$L^{YY}$-NHR, -$L^{YY}$-$NR_2$, —$CO_2H$, —$CO_2R$, -$L^{YY}$-$CO_2H$, -$L^{YY}$—$CO_2R$, -Ph, and -$L^{YY}$-Ph-, wherein $L^{YY}$ is $C_{1-3}$alkylene.

17. A method according to claim 16, wherein $L^{YY}$ is selected from —$CH_2$—, —$CH_2CH_2$—, —$CH_2CH_2CH_2$—, —$CH(CH_3)$—, —$CH(CH_3)CH_2$—, —$CH_2CH(CH_3)$—, and —$CH(CH_2CH_3)$—.

18. A method of treatment of a microbial infection in an animal, which method comprises administering to the animal a compound which is selected from:
N-(2-Aminophenyl)benzamide;
N-(2-Aminophenyl)-4-methoxybenzamide;
N-(2-Aminophenyl)-4-nitrobenzamide;
Benzyl (4-((2-aminophenyl)carbamoyl)-benzyl)carbamate;
Pyridin-3-ylmethyl (4-((2-aminophenyl)-carbamoyl)benzyl)carbamate;
Methyl 2-(4-((4-((2-aminophenyl) carbamoyl)benzyl)carbamoyl)-1H-1,2,3-triazol-1-yl)acetate;
$N^1$-(2-aminophenyl)-$N^4$-(4-(dimethylamino)phenyl)terephthalamide;
$N^1$, N 4-bis(2-aminophenyl)terephthalamide;
N 1-(2-aminophenyl)-$N^5$-(4-(dimethylamino)-phenyl)glutaramide; and
(9 H-fluoren-9-yl)methyl (4-((2-aminophenyl)carbamoyl)-benzyl)carbamate.

19. A method according to claim 1, wherein said microbial infection is selected from the group consisting of bacterial, viral, protozoal and fungal infections.

20. A method according to claim 19, wherein said microbial infection is caused by a microbial species of a genus selected from the list consisting of: *Yersenia, Salmonella, Shigella, Campylobacter, Clostridium; Heliobacter; Mycobacterium, Pseudomonas, Haemophilus, Moraxella, Escherichia, Neisseria, Streptococcus* and *Staphyllococcus*.

21. A method according to claim 19, wherein said microbial species is selected from the list consisting of: *Yersenia enterocolitica, E. Coli, Clostridium difficile, Helicobacter pylori, Mycobacterium tuberculosis, Haemophilus influenza, Moraxella catarrhalis, Pseudomonas aeruginosa, Staphyllococcus aureus*, Group A and B *Streptococcus*, HIV, RSV, influenza virus, Herpes and Hepatitis viruses.

22. A method according to claim 1, wherein said compound is used to boost the innate antimicrobial defence and\or stimulating autophagy system in an organ selected from the list consisting of: skin, eye, lung, trachea, urinary tract or kidney, genital tract, GI tract and\or blood.

23. A method according to claim 1, wherein said microbial infection results in a disorder selected from the list consisting of: gastrointestinal disorder; eye infection; urinary tract infection; genital infection; respiratory tract infection; skin infection; blood infection.

24. A method according to claim 23, wherein the gastrointestinal disorder is selected from the list consisting of: shigellosis; traveller's diarrhoea, endemic diarrhoea, dysentery, viral gastroenteritis, parasitic enteritis, Crohn's disease, ulcerative colitis, irritable bowel syndrome, precancerous states of the gastrointestinal tract, cancer of the gastrointestinal tract, diverticulitis, post-antibiotic diarrhoea, *Clostridium difficile* colitis, lactose intolerance, flatulence, gastritis, esophagitis, heartburn, gastric ulcer, ulcers associated with *Helicobacter pylori*, duodenal ulcer, short bowel syndrome, dumping syndrome, gluten enteropathy;
eye infections optionally selected from conjunctivitis, stye, blepharitis, cellulitis of the eye, keratitis, corneal ulcer, trachoma, uveitis, canaliculitis and dacryocystitis;
urinary tract and genital infections optionally selected from pyelonephritis, cystitis, gonorrhoea and urethritis;
infections of the respiratory system optionally selected from bronchitis, pneumonia, rhinosinusitis, sinusitis, pharyngitis/tonsillitis, laryngitis and influenza; tuberculosis skin infections optionally selected from boils, carbuncles, furuncles, cellulitis, abscesses, impetigo, and erysipelas.

25. A method according to claim 1, wherein the treatment is a combination treatment,
wherein the compound is used in combination with any one or more of: an antibiotic; isoleucine or active isomers or analogs thereof; a vitamin D type compound.

26. A method according to claim 1, wherein the method comprises:
(1) administration to the animal of an antibiotic for 1 or 2 days with or without the compound; followed by
(2) administration to the animal of an effective amount of the compound for a further 2, 3, 4, 5 or more days.

27. A method as claimed in claim 1, wherein the animal is a human.

* * * * *